(12) United States Patent
Cooper et al.

(10) Patent No.: US 7,815,806 B2
(45) Date of Patent: Oct. 19, 2010

(54) PURIFICATION OF FLUIDS WITH CARBON NANOTUBES HAVING ATTACHED FUNCTIONAL GROUP

(76) Inventors: Christopher H. Cooper, 40 the Village Green, Windsor, VT (US) 05089; Alan G. Cummings, 46 Reeves Rd., Hartland, VT (US) 05049; Mikhail Y. Starostin, 44 E. Wheelock St., Hanover, NH (US) 03755; Charles P. Honsinger, 48 Autumn La., Windsor, VT (US) 05089

( * ) Notice: Subject to any disclaimer, the term of this patent is extended or adjusted under 35 U.S.C. 154(b) by 742 days.

(21) Appl. No.: 11/734,858

(22) Filed: Apr. 13, 2007

(65) Prior Publication Data

US 2008/0041791 A1   Feb. 21, 2008

Related U.S. Application Data

(62) Division of application No. 10/794,056, filed on Mar. 8, 2004, now Pat. No. 7,211,320.

(60) Provisional application No. 60/452,530, filed on Mar. 7, 2003, provisional application No. 60/468,109, filed on May 6, 2003, provisional application No. 60/499,375, filed on Sep. 3, 2003.

(51) Int. Cl.
 *B32B 3/26* (2006.01)
 *B01D 15/00* (2006.01)
 *B01D 59/26* (2006.01)

(52) U.S. Cl. .................. 210/660; 210/691; 96/108; 428/315.5

(58) Field of Classification Search .............. 210/660, 210/691; 96/108; 428/315.5
See application file for complete search history.

(56) References Cited

U.S. PATENT DOCUMENTS

| 5,653,951 | A | * | 8/1997 | Rodriguez et al. | .......... 423/439 |
| 5,698,175 | A | | 12/1997 | Hiura et al. | |
| 5,846,658 | A | * | 12/1998 | Tennent et al. | .............. 428/408 |
| 5,985,112 | A | | 11/1999 | Fischer | |

(Continued)

FOREIGN PATENT DOCUMENTS

| EP | 1 092 680 A1 | 4/2001 |
| WO | WO 232558 A1 * | 4/2002 |

OTHER PUBLICATIONS

J. Zhang et al., Effect of Chemical Oxidation on the Structure of Single-Walled Carbon Nanotubes, J. Phys. Chem. B, 107, 3712 (2003).*
European Search Report for EP 07014878.

*Primary Examiner*—Chester T Barry
(74) *Attorney, Agent, or Firm*—Finnegan, Henderson, Farabow, Garrett & Dunner

(57) ABSTRACT

Disclosed herein is a nanostructured material comprising defective carbon nanotubes chosen from impregnated, functionalized, doped, charged, coated, and irradiated nanotubes, and combinations thereof. The defective carbon nanotubes contain a defect which is a lattice distortion in at least one carbon ring. Also disclosed is a method of purifying fluids, such as liquids, including water, as well as gases, including the air using, this nanostructured material.

21 Claims, 21 Drawing Sheets

U.S. PATENT DOCUMENTS

| | | | |
|---|---|---|---|
| 6,157,043 A | 12/2000 | Miyamoto | |
| 6,203,814 B1 | 3/2001 | Fisher et al. | |
| 6,331,265 B1 | 12/2001 | Dupire et al. | |
| 6,333,016 B1 | 12/2001 | Resasco et al. | |
| 6,346,136 B1 | 2/2002 | Chen et al. | |
| 6,346,189 B1 | 2/2002 | Dai et al. | |
| 6,350,488 B1 | 2/2002 | Lee et al. | |
| 6,413,487 B1 | 7/2002 | Resasco et al. | |
| 6,420,293 B1 | 7/2002 | Chang et al. | |
| 6,432,177 B1 | 8/2002 | Dallas et al. | |
| 6,432,866 B1 | 8/2002 | Tennent et al. | |
| 6,455,021 B1 | 9/2002 | Saito | |
| 6,468,930 B2 | 10/2002 | Kruszewski | |
| 6,471,936 B1 | 10/2002 | Chen et al. | |
| 6,495,116 B1 | 12/2002 | Herman | |
| 6,495,258 B1 * | 12/2002 | Chen et al. | 428/408 |
| 6,521,321 B2 | 2/2003 | Kahlbaugh et al. | |
| 6,536,605 B2 | 3/2003 | Rice et al. | |
| 6,596,055 B2 * | 7/2003 | Cooper et al. | 95/116 |
| 6,673,136 B2 | 1/2004 | Gillingham et al. | |
| 6,673,392 B2 | 1/2004 | Lee et al. | |
| 6,692,715 B2 | 2/2004 | Barbeau | |
| 6,797,167 B2 | 9/2004 | Koslow | |
| 6,818,821 B2 | 11/2004 | Fujieda et al. | |
| 6,838,005 B2 | 1/2005 | Tepper et al. | |
| 6,841,075 B2 | 1/2005 | Penth et al. | |
| 6,921,575 B2 | 7/2005 | Horiuchi et al. | |
| 6,967,013 B2 | 11/2005 | Someya et al. | |
| 7,014,681 B2 * | 3/2006 | Noack et al. | 95/54 |
| 7,014,952 B2 | 3/2006 | Shiraishi et al. | |
| 7,105,596 B2 | 9/2006 | Smalley et al. | |
| 7,138,100 B2 | 11/2006 | Smalley et al. | |
| 7,214,360 B2 | 5/2007 | Chen et al. | |
| 2001/0003082 A1 | 6/2001 | Kahlbaugh et al. | |
| 2001/0024633 A1 | 9/2001 | Lee et al. | |
| 2002/0023874 A1 | 2/2002 | Penth et al. | |
| 2002/0063093 A1 | 5/2002 | Rice et al. | |
| 2002/0106958 A1 | 8/2002 | Kruszewski | |
| 2002/0148776 A1 | 10/2002 | Cousart et al. | |
| 2002/0172639 A1 | 11/2002 | Horiuchi et al. | |
| 2002/0192142 A1 * | 12/2002 | Tillotson et al. | 423/447.1 |
| 2002/0193030 A1 | 12/2002 | Yao et al. | |
| 2003/0026985 A1 * | 2/2003 | Greiner et al. | 428/373 |
| 2003/0035769 A1 * | 2/2003 | Moy et al. | 423/447.2 |
| 2003/0037675 A1 | 2/2003 | Gillingham et al. | |
| 2003/0044339 A1 | 3/2003 | Barbeau | |
| 2003/0082979 A1 | 5/2003 | Bean et al. | |
| 2003/0111404 A1 | 6/2003 | Koslow | |
| 2003/0118727 A1 | 6/2003 | Ting et al. | |
| 2003/0118907 A1 | 6/2003 | Shiraishi et al. | |
| 2003/0127393 A1 | 7/2003 | Tepper et al. | |
| 2003/0129119 A1 | 7/2003 | Chiu et al. | |
| 2003/0129122 A1 | 7/2003 | Chen et al. | |
| 2003/0147801 A1 | 8/2003 | Someya et al. | |
| 2003/0147802 A1 | 8/2003 | Smalley et al. | |
| 2003/0148086 A1 | 8/2003 | Pfefferle et al. | |
| 2003/0155143 A1 | 8/2003 | Fujieda et al. | |
| 2003/0164427 A1 | 9/2003 | Glatkowski et al. | |

* cited by examiner

PURIFICATION OF FLUIDS WITH CARBON NANOTUBES HAVING ATTACHED FUNCTIONAL GROUP

This is a division of application Ser. No. 10/794,056, filed Mar. 8, 2004, now U.S. Pat. No. 7,211,320, which claims the benefit of U.S. Provisional Application Nos. 60/452,530, filed Mar. 7, 2003; 60/468,109, filed May 6, 2003; and 60/499,375, filed Sep. 3, 2003, all of which are incorporated herein by reference.

The present disclosure relates to a nanostructured material comprising defective carbon nanotubes chosen from impregnated, functionalized, doped, charged, coated, and irradiated nanotubes. The present disclosure also relates to the purification of fluids, such as liquids and gases, using the nanostructured material. The present disclosure also relates to the purification of water using the nanostructured material.

There are many procedures and processes to treat fluids for consumption, use, disposal, and other needs. Among the most prevalent are pasteurization to sterilize foodstuffs, chemical treatments to sterilize water, distillation to purify liquids, centrifugation and filtration to remove particulates, decanting to separate two phases of fluids, reverse osmosis to desalinate liquids, electrodialysis to desalinate liquids, and catalytic processes to covert undesirable reactants into useful products. Each of these methods is well-suited for particular applications so usually a combination of methods is used for a final product.

One promise of nanotechnology materials is that they will help do things more cost-effectively than their traditional counterparts. In the area of liquid purification, any technology that can lower the overall cost, simplify a process, and improve efficiencies would be very advantageous.

Many of these processes would be improved by using nanomaterial purification technologies. Nanoporous materials would be useful to remove microorganisms, micron size particulates, and other very fine materials. Reverse osmosis membranes made with nanomaterials could help improve the flow of water through the membrane. Incorporating strong nanomaterials into any of the above processes would lower the weight of all of these components. But two processes seem especially likely for nanomaterial fluid purification: sterilization and desalination.

Sterilization

There are many different technologies available for the sterilization of liquid. Adsorption, chemical treatments, ozone disinfection, and UV irradiation all perform very well for the removal of pathogenic microbes. However, each of these technologies has limitations, including overall efficacy, initial & operating cost, byproduct risk, necessary pre-treatment of liquid, hazardous compounds used or produced, and other limitations.

Although chemical methods are the most widespread in use, they have a number of shortcomings. Such drawbacks include increasing microbiological adaptation to their destructive effects (e.g. *Cryptosporidium parvum*), safety hazards associated with chlorine use and storage, and environmental impact. UV is gaining in popularity but the liquid must be clear in order for it to be effective, it does not break down any biofilm formation, and it is very expensive to install and operate.

In industrial and municipal applications such as water and wastewater plants, the three most widely used methods of liquid sterilization are: ozone, chlorine, and ultraviolet irradiation. Recent publications of the U.S. Environmental Protection Agency have identified the pros and cons of each method.

Ozone is more effective than Chlorine at destroying viruses and bacteria, has a short contact time (10-30 minutes) for effectiveness, leaves no harmful residuals as it breaks down quickly, and is generated onsite so there are no transportation risks. On the other hand, at low dosages ozone may not be effective, it is more complex than either UV or chlorine, it is very reactive and corrosive, it is toxic, capital costs can be high and power requirements can be high.

Chlorine is more cost-effective than ozone or UV, its residual can prolong disinfection, it is reliable and effective against a range of pathogenic organisms, and it offers flexible dosing control. Chlorine, though, carries with it significant risks including the facts that chlorine residual is toxic to aquatic life, chlorine is corrosive and toxic, chlorine's oxidation of organic matter creates hazardous compounds, and some parasitic species have shown resistance. In addition, chlorine can bind with natural organic material to create carcinogenic compounds hazardous for consumption.

Ultraviolet irradiation has been used for some time because it effectively inactivates most spores, viruses, and cysts, eliminates risks of handling chemicals, leaves no residual that can be harmful, is user-friendly to operators, requires a very short contact time (20-30 seconds) for effectiveness and requires less space. The downsides of UV irradiation include: that at low dosages it may not be effective; that organisms can sometimes reverse and repair UV damage; that tubes can foul requiring frequent preventative maintenance; that turbidity can render UV ineffective, the energy requirements are very high. Further, disposal of hazardous UV lamps can be expensive.

In response to the shortcomings of known disinfection methods, a number of new approaches have been tried. For example, U.S. Pat. No. 6,514,413, which is herein incorporated by reference, discloses using a composite, bactericidal adsorption material. Such bactericidal adsorption material, however, have been shown to be prone to biofouling and bacterial grow-through for continued reproduction. U.S. patent application Ser. No. 09/907,092 discloses a portable oxidant generator for generating a chlorine or chlor-oxygen solution for sterilizing contaminated drinking water. U.S. Pat. No. 6,495,052 discloses a system and method for treatment of water that introduces a bactericide into the water and then removes it prior to consumption. U.S. patent application Ser. No. 10/029,444 discloses a method whereby water is subjected to light from a laser as means of disinfection.

Again, however, these approaches rely on high inputs of electricity, toxic chemicals, or long contact times for effectiveness. What is still needed is a method that has minimal energy requirements, utilizes no toxic chemicals, and requires a very short contact time, and can be embodied into a portable device.

Desalination

Desalination of liquids would be highly useful for drinking water, biological fluids, medicines, chemicals, petroleum and its derivatives, and many other liquids. In addition, desalination of water would be beneficial since less than 0.5% of the Earth's water is directly suitable for human consumption, agricultural, or industrial uses. Consequently, desalination is finding increasing favor throughout the world to produce potable water from brackish groundwater and seawater since it makes the other approximately 99.5% of the water available.

There are an estimated 4,000 water desalination plants worldwide with a combined capacity of over 3,500 million gallons per day (mgd). About 55% of this capacity is in the Middle East and 17% is in the U.S., many of which are for industrial use. Desalinated water now accounts for about 1.4% of the water consumed in the United States for domestic and industrial purposes.

There are essentially five basic desalination methods: thermal, reverse osmosis, electrodialysis, ion exchange, and freezing. Thermal and freezing processes remove fresh water from saline leaving behind concentrated brine. Reverse osmosis and electrodialysis employ membranes to separate salts from fresh water. Ion exchange involves passing salt water over resins which exchange more desirable ions for less desirable dissolved ions. Only thermal and reverse osmosis processes are currently commercially viable.

As explained in U.S. Pat. Nos. 5,217,581 and 6,299,735, which are herein incorporated by reference, thermal processes involve boiling or otherwise evaporating salt water and condensing the vapor as fresh water, leaving behind a more concentrated brine solution. The energy requirement for distillation is relatively high compared to other methods. In part because the energy required for distillation does not increase appreciably with increasing salinity of the feed water, it is widely used in the Middle East to treat seawater.

As described in U.S. Pat. No. 3,462,362, reverse osmosis is a membrane process that employs the tendency for fresh water to pass through a semipermeable membrane into a salt solution, thereby diluting the more saline water. The fresh water moves through the membrane as though there were pressure on it, which is called osmotic pressure. By applying very high pressure to saline water on one side of a semipermeable membrane, fresh water can be forced through the membrane in the direction opposite that of the osmotic flow. This process is called reverse osmosis. Although it is energy intensive (to create the high pressure), the energy requirements of reverse osmosis are generally lower than those of distillation although its use of feed water is more inefficient than other methods. Additionally, the membranes are very expensive, delicate, and prone to fouling.

Desalination by electrodialysis is a membrane process that removes contaminants and salt from liquids by using an electric current to pull ionic impurities through ion selective membranes and away from the treated liquids. Two types of ion-selective membranes are used—one allows passage of positive ions and one allows passage of negative ions between the electrodes of an electrolytic cell. Electricity is used to overcome the resistance of the ion through the ion selective membrane. The greater the resistance the higher the power demand, and hence the energy cost will increase as the resistance increases. When an electric current is applied to drive the ions, fresh liquid is left between the membranes. The amount of electricity required for electrodialysis, and therefore its operating cost, increases with increasing salinity of feed liquid.

Ion exchange resins replace hydrogen and hydroxide ions with salt ions. A number of municipalities use ion exchange for water softening, and industries commonly use ion exchange resins as a final treatment following reverse osmosis or electrodialysis to produce very pure water. The primary cost of ion exchange is in maintaining or replacing the resins. The higher the concentration of dissolved salts in the water, the more often the resins will need to be regenerated and consequently ion exchange is rarely used for salt removal on a large scale.

Freezing processes involve three stages: partial freezing of the salt water in which ice crystals of fresh water are formed, separating these ice crystals from the brine, and then melting the ice crystals (e.g., U.S. Pat. No. 4,199,961). Freezing has some advantages over other processes as it requires less energy and its low operating temperatures minimize corrosion and scale formation problems. The energy requirements of freezing processes are high and are generally comparable to those of reverse osmosis. Freezing technologies are still being researched and developed and are not widely deployed. Freezing technology is not a compatible technology for portable desalinization devices.

There have also been a number of capacitors invented for the purpose of desalination. U.S. Pat. No. 4,948,514 discloses a method and apparatus for separating ions from liquid. U.S. Pat. No. 5,192,432 discloses a similar "flow-through capacitor" method for separating ions from liquid. However, these devices have not found wide-scale use because they are not economically viable.

SUMMARY OF INVENTION

The present disclosure solves the aforementioned problems as it relates to fluid purification methods based on nanotechnology materials. One aspect of the present disclosure is related to a nanostructured material comprising defective carbon nanotubes chosen from impregnated, functionalized, doped, charged, coated, and irradiated nanotubes. "Nanostructured" refers to a structure on a nano-scale (e.g., one billionth of a meter), such as on the atomic or molecular level. "Nanostructured material" is a material comprising at least one of the above-mentioned carbon nanotube components. "Nanomembrane" is a membrane composed of the nanostructured material. Defective carbon nanotubes are those that contain a lattice distortion in at least one carbon ring. A lattice distortion means any distortion of the crystal lattice of carbon nanotube atoms forming the tubular sheet structure. Non-limiting examples include any displacements of atoms because of inelastic deformation, or presence of 5 and/or 7 member carbon rings, or chemical interaction followed by change in $sp^2$ hybridization of carbon atom bonds.

Another aspect of the invention is directed to elongated nanotubes consisting essentially of carbon, wherein the nanotube is distorted by crystalline defects, similar to those described above. In this embodiment, the nanotubes are distorted, due to the defects, to a degree that the nanotubes, when treated, have significantly greater chemical activity that allow the nanotube to react with, or bond to, chemical species that would not react with or bond to undistorted and/or untreated nanotubes.

In one aspect of the invention, the carbon nanotubes are present in the nanostructured material in an amount sufficient to substantially destroy, modify, remove, or separate contaminants in fluid that comes into contact with the nanostructured material. The carbon nanotubes are treated to achieve such properties. For example, chemical treatments of the carbon nanotubes can lead to the resulting nanotubes having at least one end which is at least partially open. Nanotubes having such ends can provide unique properties, either from a fluid flow perspective or from a functionalization perspective, e.g., having the ability of that end to be particularly functionalized, for example.

In another aspect of the invention, the material that is used to impregnate, functionalize, dope, or coat the carbon nanotubes is present in an amount sufficient to achieve active and/or selective transport of fluids or components thereof into, out of, through, along or around the carbon nanotubes. This material may comprise the same material that is selectively transported into, out of, through, along or around the carbon nanotubes.

For example, a nanostructure material used to remove arsenic from fluid, can be first impregnated with arsenic ions. These arsenic ions are referred to as the "target ion." A "target ion" generally encompasses an ion that is impregnated (functionalized, doped or coated) into the carbon nanotube, and that is the same as the ion of the contaminant found in the fluid to be cleaned or purified.

As used herein, "impregnated" means that the carbon nanotubes are at least partially filled with the material of interest, which, as shown above, may comprise the same ion of the contaminant to be removed from the contaminated fluid. By impregnating a target ion into the carbon nanotubes, the nanotubes, and indeed the nanostructure made of the nanotubes, are primed or "challenged" to accept and/or attract and/or those same ions found within the contaminated fluid.

While the above example refers to impregnated ions, the same methods apply for challenging or priming the carbon nanotubes with desired ions by any of the described procedures, e.g., functionalization, doping, coating, and combination thereof. A doped carbon nanotube refers to the presence of atoms, other than carbon, in the nanostructured material.

With respect to impregnation, an ion specific separation device composed of a target ion-impregnated carbon nanotube can be fabricated. For this device, the impregnated nanotubes are fabricated such that an electron or phonon current can either be induced by electromagnetic, or acoustic means or by direct electrical or physical connection, and have defect sites that can be opened through functionalization chemistry to create ion channels.

In challenging the carbon nanotubes by at least partially filling carbon nanotubes with target contaminate ions, ion specific quantum wells will be created within the hollow region of the nanotube due to the quasi-one dimensional nature of the carbon nanotube defined by its morphology. This will create a "pre-programmed" or ion specific trap when the ion is moved or indexed through the nanotube. When the ion is moved within the nanotube, the ion specific trap is left behind, in the quasi one-dimensional quantum structure of the nanotube.

As ionic contaminated fluid comes into contact with the treated "pre-programmed" nanostructured material containing the target ions, the target ion will be able to minimize its free energy by adsorbing and filling the ion specific trap within the nanotube. The addition of the target ion in the nanotube will cause a change in resistance, which will trigger an electric and/or phononic current response that will move at least one ion through the nanotube and out of the system. The material can be programmed or reprogrammed depending on what ion the nanotube, nanostructured device has been filled with.

As the ion concentration changes, the device will not have to consume power because power is only required when target ions are present. The built in self limiting process will take advantage of the fact that when there are no target ions in the fluid no power is required to remove them.

Depending on the contaminant to be removed from the contaminated fluid, the target material or the material that is used to impregnate, functionalize, dope, or coat the carbon nanotubes may comprise at least one compound chosen from oxygen, hydrogen, ionic compounds, halogenated compounds, sugars, alcohols, peptides, amino acids, RNA, DNA, endotoxins, metalo-organic compounds, oxides, borides, carbides, nitrides, and elemental metals and alloys thereof.

The oxides comprise any well known oxide generally used in the art, such as an oxide of carbon, sulfur, nitrogen, chlorine, iron, magnesium, silicon, zinc, titanium, or aluminum.

In one aspect, the nanostructured material comprises the carbon nanotubes being placed in, and optionally dispersed in via ultrasonication, a liquid, solid, or gaseous medium. The carbon nanotubes may be maintained in such a medium by a mechanical force or a field chosen from, mechanical, chemical, electromagnetic, acoustic, and optic fields or combinations thereof. One of skilled in the art would understand that acoustic fields comprise certain frequencies of noise inside a cavity to form standing waves that hold the carbon nanotubes in a substantially static position.

Similarly, an optical field may comprise a single or an active array of optical tweezers generated by passing laser light through a hologram.

The solid medium in which the carbon nanotubes can be found generally comprises at least one component chosen from fibers, substrates, and particles, each of which may comprise metallic, ceramic, and/or polymeric materials. In a solid medium, the carbon nanotubes are interconnected and/or connected to fibers, substrates, and particles, such as those having a diameter up to 100 microns, to form a nanomembrane.

Particle size is determined by a number distribution, e.g., by the number of particles having a particular size. The method is typically measured by microscopic techniques, such as by a calibrated optical microscope, by calibrated polystyrene beads and by calibrated scanning force microscope or scanning electron microscope or scanning tunneling microscope and scanning electron microscope. Methods of measuring particles of the sizes described herein are taught in Walter C. McCrone's et al., *The Particle Atlas*, (An encyclopedia of techniques for small particle identification), Vol. I, Principles and Techniques, Ed. Two (Ann Arbor Science Pub.), which is herein incorporated by reference.

In different aspects of the present invention, the polymeric material of the solid medium comprises single or multi-component polymers (advantageously where the multi-component polymers have at least two different glass transition or melting temperatures), nylon, polyurethane, acrylic, methacrylic, polycarbonate, epoxy, silicone rubbers, natural rubbers, synthetic rubbers, vulcanized rubbers, polystyrene, polyethylene terephthalate, polybutylene terephthalate, Nomex (poly-paraphylene terephtalamide), Kevlar poly (p-phenylene terephtalamide), PEEK (polyester ester ketene), Mylar (polyethylene terephthalate), viton (viton fluoroelastomer), polyetrafluoroethylene, polyetrafluoroethylene), halogenated polymers, such as polyvinylchloride (PVC), polyester (polyethylene terepthalate), polypropylene, and polychloroprene.

The at least two different glass transition or melting temperatures of the multi-component polymers described herein are measured by heating to a temperature at which the material has inelastic deformation.

In an aspect of the invention, the ceramic material of the solid medium comprises at least one of the following: boron carbide, boron nitride, boron oxide, boron phosphate, compounds having a spinel or garnet structure, lanthanum fluoride, calcium fluoride, silicon carbide, carbon and its allotropes, silicon oxide, glass, quartz, aluminum oxide, aluminum nitride, zirconium oxide, zirconium carbide, zirconium boride, zirconium nitride, hafnium boride, thorium oxide, yttrium oxide, magnesium oxide, phosphorus oxide, cordierite, mullite, silicon nitride, ferrite, sapphire, steatite, titanium carbide, titanium nitride, titanium boride, and combinations thereof.

In another aspect of the invention, the metallic material of the solid medium comprises at least one of the following elements: aluminum, copper, cobalt, gold, platinum, silicon, titanium, rhodium, indium, iron, palladium, germanium, tin, lead, tungsten, niobium, molybdenum, nickel, silver, zirconium, yttrium, and alloys thereof, including an alloy of iron, i.e., steel.

The liquid medium in which the carbon nanotubes can be found include water, oil, organic and inorganic solvents, as well as the liquid form of nitrogen and carbon dioxide.

The gaseous medium in which the carbon nanotubes can be found include the air, or a gas chosen from argon, nitrogen, helium, ammonia, and carbon dioxide.

One aspect of the present disclosure is related to the use of carbon nanotubes that have a scrolled tubular or non-tubular nano-structure of carbon rings. These carbon nanotubes are usually single-walled, multi-walled or combinations thereof, and may take a variety of morphologies. For example, the carbon nanotubes used in the present disclosure may have a morphology chosen from nanohorns, nanospirals, dendrites, trees, spider nanotube structures, nanotube Y-junctions, and bamboo morphology. Such shapes generally tend to add in the use of the carbon nanotubes for nanomembranes. The above described shapes are more particularly defined in M. S. Dresselhaus, G. Dresselhaus, and P. Avouris, eds. Carbon Nanotubes: Synthesis, Structure, Properties, and Applications, Topics in Applied Physics. Vol. 80. 2000, Springer-Verlag; and "A Chemical Route to Carbon Nanoscrolls, Lisa M. Viculis, Julia J. Mack, and Richard B. Kaner; Science 28 Feb. 2003; 299, both of which are herein incorporated by reference.

As previously described, carbon nanotubes may be functionalized to achieve desired chemical or biological activity. As used herein, a functionalized carbon nanotube is one that comprises inorganic and/or organic compounds attached to the surface of the carbon nanotubes.

The organic compounds may comprise linear or branched, saturated or unsaturated groups. Non-limiting examples of such organic compounds include at least one chemical group chosen from: carboxyl, amine, polyamide, polyamphiphiles, diazonium salts, pyrenyl, silane and combination thereof.

Non-limiting examples of the inorganic compounds include at least one fluorine compound of boron, titanium, niobium, tungsten, and combination thereof. The inorganic compounds as well as the organic compounds may comprise a halogen atom or halogenated compound.

In an aspect of the invention, functionalized carbon nanotubes comprise any one or any combination of the above-described inorganic and organic groups. These groups are generally located on the ends of the carbon nanotubes and are optionally polymerized.

For example, the functionalized carbon nanotubes can comprise a non-uniformity in composition and/or density of functional groups across the surface of the carbon nanotubes and/or across at least one dimension of the nanostructured material. Similarly, the functionalized carbon nanotubes can comprise a substantially uniform gradient of functional groups across the surface of the carbon nanotubes and/or across at least one dimension of the nanostructured material.

According to one aspect of the disclosure, carbon nanotubes are charged, such as with an AC or DC electromagnetic field, to a level sufficient to achieve desired properties. Desired properties include facilitating the coating of a surface of the nanotubes or aiding in the destruction, modification, removal, or separation of contaminants that are found in fluids that are in contact or in proximity to the carbon nanotubes. "Removal" is understood to mean at least one of the following mechanisms: size exclusion, absorption, and adsorption.

In addition, charging may occur using any one of the following methods: chemical, irradiation, capacitive charging, or fluid flowing adjacent and/or through the carbon nanotubes. Charging of the nanotubes may occur prior to or simultaneous with the above-described functionalization procedure.

Charging the nanotubes tends to facilitate their coating with metallic and/or polymeric materials Examples of such metallic materials that can be used to coat the carbon nanotubes include gold, platinum, titanium, rhodium, iridium, indium, copper, iron, palladium, gallium, germanium, tin, lead, tungsten, niobium, molybdenum, silver, nickel, cobalt, metals of the lanthanum group, and alloys thereof.

Examples of such polymeric material that can be used to coat the carbon nanotubes include multicomponent polymers (advantageously where the multi-component polymers have at least two different glass transition or melting temperatures), nylon, polyurethane, acrylic, methacrylic, polycarbonate, epoxy, silicone rubbers, natural rubbers, synthetic rubbers, vulcanized rubbers, polystyrene, polyethylene terephthalate, polybutylene terephthalate, Nomex (polyparaphylene terephtalamide), Kevlar poly (p-phenylene terephtalamide), PEEK (polyester ester ketene), Mylar (polyethylene terephthalate), viton (viton fluoroelastomer), polyetrafluoroethylene, polyetrafluoroethylene), halogenated polymers, such as polyvinylchloride (PVC), polyester (polyethylene terepthalate), polypropylene, and polychloroprene.

When using irradiation to treat the carbon nanotubes and/or fuse the carbon nanotube nanostructured material, at least one type of particle chosen from photons, electrons, nuclear, and ion particles impinge on the carbon nanotube in an amount sufficient to break at least one carbon-carbon and/or carbon-dopant bonds, to activate the nanostructure, or to perform ion implantation.

Contaminants that can be cleaned from fluids include pathogens, microbiological organisms, DNA, RNA, natural organic molecules, molds, fungi, natural and synthetic toxins (such as chemical and biological warfare agents), heavy metals (such as arsenic, lead, uranium, thallium, cadmium, chromium, selenium, copper, and thorium), endotoxins, proteins, enzymes, and micro and nano-particle contaminants.

The present disclosure also relates to a method of purifying fluids, which includes both liquids and gases by removing at least one of these contaminants from fluid. In such a method, contaminated fluid is contacted with the above described nanostructured material, e.g., the nanostructured material comprising defective carbon nanotubes chosen from impregnated, functionalized, doped, charged, coated, and irradiated nanotubes, and combination thereof.

According to a method described herein, the activated nanostructured material may be treated and/or activated with constituents that modify the biological or chemical activity of the fluid to be cleaned.

In addition, the method allows for at least partially separating contaminants from the treated fluids to form distinct fluid streams of contaminants and treated fluid.

In one embodiment, the fluid to be cleaned is a liquid, such as water, natural and/or synthetic petroleum and its byproducts, biological fluids, foodstuffs, alcoholic beverages, and medicines.

With respect to petroleum products, one major problem is the latent growth of bacteria in the petroleum during storage. This has been a problem particularly with aviation fuel. The presence of such bacteria can severely foul and eventually ruin the fuel. Accordingly, a major area of concern in the area of liquid purification is for cleaning bacteria from natural and/or synthetic petroleum products. Natural and/or synthetic petroleum and its byproducts include aviation, automotive, marine, and locomotive fuels, rocket fuels, industrial and machine oils and lubricants, and heating oils and gases.

The biological fluids described herein are derived from an animal, human, plant, or comprise a growing broth used in the processing of a biotechnology or pharmaceutical product. In one embodiment, the biological fluids comprise blood, human milk and components of both.

In another embodiment, foodstuffs comprise animal by-products, such as eggs and milk, fruit juice, natural syrups, and natural and synthetic oils used in the cooking or food industry, including, but not limited to olive oil, peanut oil, flower oils (sunflower, safflower), vegetable oil, and the like.

In addition to foodstuffs, one embodiment of the present invention involves the treatment of alcoholic beverages. By its very nature, the fermentation of alcoholic beverages results in contaminants in the finished product. For example, oxygen is one undesired contaminant of the wine making process. As oxygen can cause the wine to spoil while in the bottle, sulfites are normally added to absorb or remove this excess oxygen. Due to health concerns, however, sulfites should be avoided. One aspect of the present invention includes treating wine to remove unwanted contaminants, such as oxygen, using the above-describe nanostructure material. Because the process would eliminate or substantially reduce the need for sulfites in wine, the wine industry would benefit from the purification process described herein.

Another aspect of the present invention includes a method of cleaning the air to remove the above-mentioned contaminants.

The present disclosure also relates to a method of purifying water by contacting contaminated water with an activated nanostructured material described herein. It has been demonstrated that contaminants, such as salts, bacteria and viruses, can be removed from water, to a level of at least 3 logs (99.9%), such as at least 4 logs (99.99%), and at least 5 logs (99.999%), and up to level of detection currently available, i.e., up to 7 logs (99.99999%).

The contaminants again comprise pathogens, microbiological organisms, DNA, RNA, natural organic molecules, molds, fungi, natural and synthetic toxins, heavy metals (e.g., arsenic, lead, uranium, thallium, cadmium, chromium, selenium, copper, and thorium), endotoxins, proteins, enzymes, and micro and nano-particle contaminants. Also of interest is the desalination of water (i.e., where the contaminants comprise salts).

DETAILED DESCRIPTION OF INVENTION

Fluid Sterilization

Figure 1:
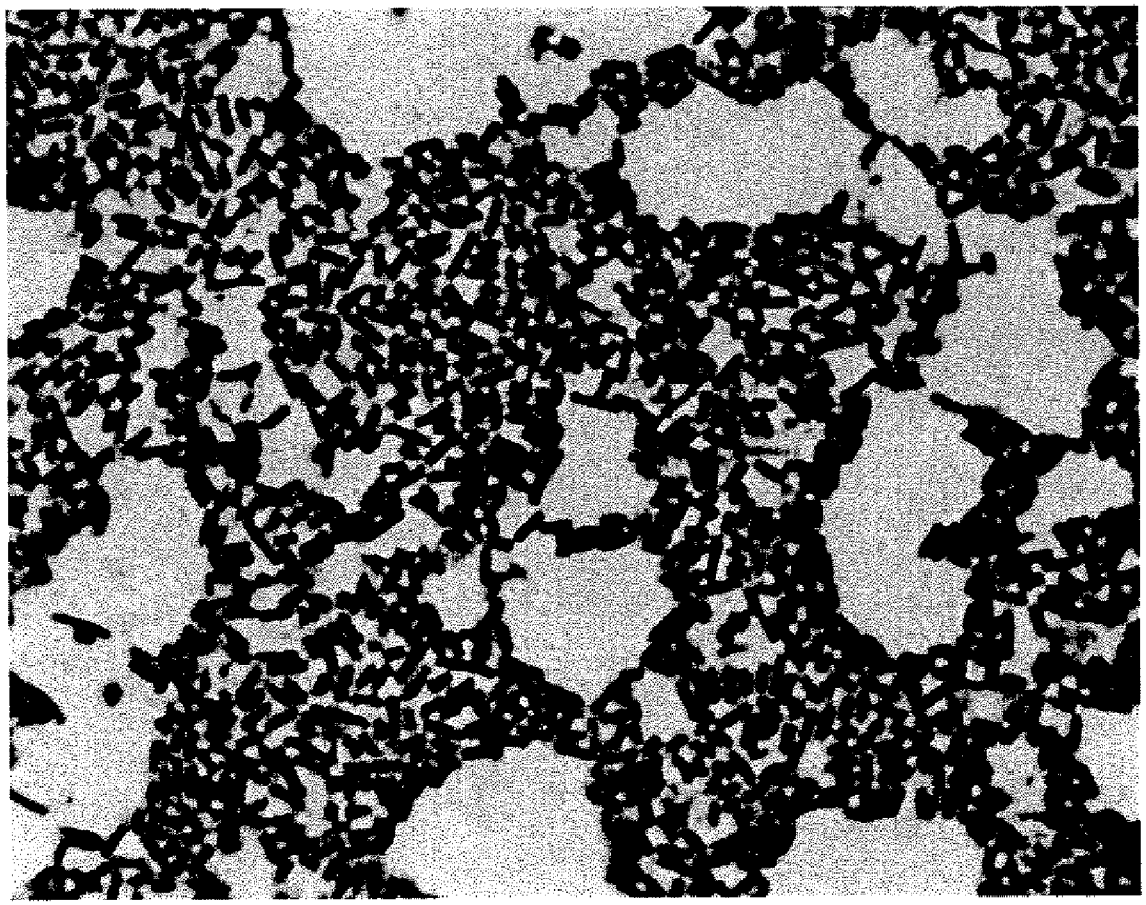
FIG. 1 is an optical image of sample 1: *E. coli* without carbon nanotube, nanostructured material (not sonicated; fixation after 48 hours).

As described herein, fluid sterilization incorporating nanostructures such as carbon nanotubes, metallic oxide nanowires, and metal nanowires is believed to be a result, at least in part from, in the formation of a unique nanoscopic kill zone that uses focused forces to kill microbes and other pathogens.

For example, it is believed that during sterilization of fluids, microorganisms come into contact with the nanomaterial described herein, causing focused forces to be applied to the microorganisms which break open cell membranes and cause internal cellular damage, thus destroying the microorganisms or destroying their ability to reproduce. In this way, liquids can be sterilized from microorganisms. Common microorganisms are 1-5 microns long and as such are at least 100 times larger than a nanostructure such as carbon nanotubes. Known examples of these organisms include *E. coli, Cryptosporidium parvum, Giardia lamblia, Entamoeba histolytica*, and many others.

Due to the large size differences, forces on the nanoscopic scale, can be applied that are many times, e.g., by orders of magnitude, more concentrated than those based on microscopic technologies. In much the same way that focused light gives the intensity to a laser, focused forces give the intensity to nanoscale destruction of microbes. Thus, mechanical and electrical forces that are on other scales either too small to be effective or very energy-intensive, on the nanoscale can be used to effectively and efficiently destroy microorganisms.

Mechanisms believed to be capable of destroying microorganisms in this nano-regime can act independently or in concert with one another. Non-limiting examples of such mechanisms include:

Mechanical destruction of the cell wall through focused forces, much like a pin breaking a balloon;

Vibrational waves causing internal cellular damage to the DNA, RNA, proteins, organelles, etc.;

Vibrational waves causing damage to the cell wall and transport channels;

Van der Waals forces;

Electromagnetic forces;

Damaging of the cell walls and DNA through the disruption of hydrogen bonding in the vicinity of nanostructures; and Bubble cavitations from shockwaves in the liquid which damage the cell structure.

Since the osmotic pressure within a typical microbial cell is higher than that of the surrounding fluid, assuming non-physiological conditions, even slight damage to the cell wall can cause total rupture as the contents of the cell flow from high to low pressure.

MS2, which is commonly used as a surrogate in assessing treatment capabilities of membranes designed for treating drinking water, is a single stranded RNA virus, with a diameter of 0.025 um and an icosahedron shape. Its size and shape are similar to other water related viruses such as the poliovirus and hepatitis.

Liquid Desalination

A process of liquid desalination according to the present disclosure is also based on nanomaterials such as carbon nanotubes, metallic oxide nanowires, and metal nanowires. One mechanism believed to be capable of desalinating liquid with nanomaterials is the creation of an ionic separation gradient between two nanomaterial membranes. When one nanomaterial membrane carries a positive charge and the other membrane a negative charge, the charge difference between these two plates creates an ionic separation gradient that causes cations to migrate to one side of the zone and anions to migrate towards the other. The tremendous surface area on the nanomaterial membranes is used to create very high capacitance, enabling the creation of a very efficient ionic gradient.

A desalination unit could incorporate two or more parallel layers of supported conductive nanomaterial membrane that are electrically isolated from each other. This layered nanostructured material may be assembled at the intersection of a Y junction channel. The two or more layers may be electrically charged, in a static mode, or in an active mode in which the charge on each plate sequentially indexes from positive to neutral to negative to neutral—one positively and one negatively—to create either a salt trap between them or to electronically create a moving capacitor in the structure causing the salt to migrate in a different direction than the flow of the water. The concentrated salt water would be channeled out one leg of the Y junction and the fresh water out the other.

The geometry, capacitance, and morphology of the device may be optimized for the hydrodynamic flow using complex analysis such as method of residues, fitness functions and optimization algorithms. The base unit of the device will be a variant on the wide junction geometry in which most of the liquid will continue to flow along the main channel while a smaller quantity of liquid is taken out through the outlet channel.

Many such base units may be used in parallel and/or series to reduce the salt concentration and increase total liquid processed. To further concentrate the salt-liquid runoff it is envisioned to use a heat pump to cool the near super-saturated salt liquid and to heat the incoming raw liquid. Such a system can be actively monitored to ensure proper concentration before cooling is applied. Salt crystallization will occur when the solution is cooled because the saturated solution will transition into a super-saturated state more quickly in colder temperature. In salt water, this will have the effect of speeding the crystallization of the salt in the brine.

The final products of the desalination process will be a nearly salt free liquid, such as removing contaminants, including but not limited to crystallized salts or a concentrated brine mixture, to a level of at least log 4 (99.99%) and up to and including log 7 (99.99999), with intermediate levels of log 5 and log 6 purity. In one embodiment, a refrigerated brine holding tank will speed crystallization and allow any remaining liquid to be put through the process again.

According to one aspect of the present disclosure, surfaces susceptible to biomaterials and other impurities or contaminants can be coated in a layer of nanomaterial to prevent the growth of microbes. Non-limiting examples of such nanomaterials include functionalized nanotube nanostructured material that have been functionalized with elements or compounds having antibacterial properties, such as silver, or aluminum oxide.

The invention further relates to methods to the manufacture the nanostructure materials described herein. Such methods include an organic solvent evaporation process, a metallic oxide nanowire process, a geometric weave process, a vacuum filtration process, and a nanostructure polymerization process. Each of these processes can create a nanostructure with nanomaterials embedded on them or composed of them. And each of these membranes enables the fluid purification treatment technologies disclosed herein.

In one embodiment, membranes made according to the present disclosure has high permeability to allow for high fluid flow rates. The permeability of a nanomaterial membrane is generally controlled by its thickness and fiber density. Accordingly, an ultrathin, ultrastrong nanomaterial membrane of low fiber density will be much more transparent to the flow of fluids than a thick nanomaterial membrane would be. Therefore, one embodiment of the present invention is directed to a fused nanomaterial membrane primarily composed of high strength carbon nanotubes.

To enhance its structural support and binding to other entities, the entire nanomaterial membrane can be coated with a metal, a plastic, or a ceramic. Defects can be removed from the nanomaterial membrane by chemical, electrical, thermal, or mechanical means to enhance its structural integrity.

The entire nanomaterial membrane can be stimulated with static or dynamic electromagnetic fields to cause specific absorption or rejection of certain molecules when fine tuned. High-frequency electrical stimulation can create an ultrasonic self-cleaning effect. By taking advantage of the strength, Young's modulis, conductivity, and piezo-electric effect of the nanotube, nanostructured material one can stimulate the material as a whole to vibrate, and to eject contaminates from the surface, so as to reduce fouling.

The starting carbon nanotubes generally contain residual iron particles or other catalytic particles that remain after production of the nanotubes. In certain embodiments, it is desired to wash the carbon nanotubes with a strong oxidizing agent such as acids and/or peroxides or combinations there of before forming a nanostructured material. Upon washing with a strong oxidizing agent, the iron generally found in the carbon nanotubes is oxidized to $Fe^{++}$ and $Fe^{+++}$. In addition, acid washing has the benefit of removing amorphous carbon which interferes with the surface chemistry of the nanotube.

It is believed that the passivated, or positively charged iron plays a role in the removal of micro organisms which are known to have a net negative charge. Under this theory, the micro-organisms are attracted to the functionalized positively charged nanotube. The resulting electric field of the now charged carbon nanotubes, which are partially filled and doped with iron, will destroy biological pathogens. Any positively charged hydrogen ions left over from the acid wash and trapped inside the nanotube will also contribute to the electric field.

It is also thought that this acid washing procedure contributes to the high degree of hydrophilicity of these functionalized carbon nanotubes and the resulting carbon nanostructured material. The washed carbon nanotubes are generally fabricated into a nanostructured material using one of the following processes. It is noted that any one of the following processes, as well as those described in the Examples, can be used to create a nanostructured material described herein, whether multi or monolayered.

Organic Solvent Evaporation Process

In the Organic Solvent Evaporation Process, a nanostructure material, such as a sterilization membrane, can be made by bonding nanomaterials with an adhesive. Examples of adhesives are chemical adhesives, such as glue, metallic adhesives, such as gold, and ceramic adhesives, such as alumina. Examples of nanomaterials are carbon nanotubes, silicon and other metallic nanowires, and metallic oxide nanowires.

According to this process, carbon nanotubes can be mixed with a solvent, such as xylene. In one embodiment, this dispersion is next be placed in an ultrasonic bath for 5-10 minutes to de-agglomerate the carbon nanotubes. The resulting dispersion is next poured onto fiber paper to allow the organic solvent to evaporate, optionally with the addition of moderate heating. Upon evaporation, the carbon nanotubes deposit on the fiber paper. Additionally, other polymeric materials may be added to the organic solvent to enhance the resulting structure's mechanical stability, the concentration of this adhesive material can be at 0.001-10% of the weight of the solvent used.

Metallic Oxide Nanowire Process

In another aspect of the present disclosure, a sterilization membrane is made with metallic oxide nanowires. In this type of process, metal meshes are heated to a temperature ranging from 230-1000° C. in an oxidative environment to create metallic oxide nanowires on the metal wires of the metal mesh. The metal meshes may comprise a metal chosen from copper, aluminum, and silicon. The metallic oxide nanowires can be in a size ranging from 1-100 nanometers in diameter, such as 1-50 nanometers in diameter, including 10-30 nanometers in diameter. Advantageously, the surface of the mesh is abraded to provide surface texture to accept and hold the nanotube aliquot deposition to create better substrate attachment.

A membrane made according to this process may be used by itself to sterilize liquid, treated to strengthen its overall structure, or coated with carbon nanotubes or other nanostructures for further activity. In the coatings of carbon nanotubes, solutions of well-dispersed single or multi-walled carbon nanotubes are passed through the mesh where they adhere to the metallic oxide surface. This resulting mesh may or may not be treated thermally, mechanically (e.g., such as by hydraulic pressure), chemically, or through rapid laser heating to enhance structural integrity. It also may or may not be coated with metal, ceramic, plastic, or polymers to enhance its structural activity. The resulting mesh may also be subjected to this nanotube solution treatment a number of times until the proper design criteria are reached. Further modification to the carbon nanotubes and/or support of this membrane can be made to functionalize the materials so that they chemically react with biological molecules to destroy, modify, remove, or separate them.

In this process, metal meshes, such as copper meshes are placed in a chemical vapor deposition chamber in an oxidative environment. The reaction zone is heated to a temperature ranging from 230-1000° C. to cause creation of metallic oxide nanowires while the chamber is in an atmosphere for a period ranging from 30 minutes to 2 hours. In certain embodiments, a dispersion of carbon nanotubes in liquid can then passed through the formed structure. After this treatment, the entire structure can be thermally annealed in vacuum at 1000° C. to strengthen the overall structure. The carbon nanotubes can optionally be treated in a solution of nitric and sulfuric acids to create carboxyl functional groups on the carbon nanotubes.

Deposition Process

In this process, a sterilization membrane can be made by vacuum deposition of carbon nanotube dispersions to lay down layers of carbon nanotubes on at least one substrate. Ultrasonication may be used to aid in dispersing and/or deagglomerating carbon nanotubes during deposition.

An envisioned process of the deposition method comprises placing carbon nanotubes in a suitable organic solvent or liquid and ultrasonicating to disperse the carbon nanotubes during deposition. The solution can be placed in a vacuum filtration device equipped with ultrasonication to further ensure that the carbon nanotubes are deagglomerated. The nanomaterial in the solution may be deposited on to a substrate whose porosity is small enough to trap carbon nanotubes but larger than the microorganisms to be removed from the contaminated fluid. The resulting NanoMesh™ can be removed with the help of using a supporting metal mesh to maintain flatness during removal. The porous substrate used to trap the carbon nanotubes can also be removed by dissolving in acid or base, or oxidized to leave a free-standing carbon nanotube membrane.

According to an aspect of the present disclosure, the vacuum filtration process may be modified by using electromagnetic fields to align the nanostructures during deposition. As in the previously described process, the nanostructures are placed in a suitable solvent (organic solvent or liquid), ultrasonicated to disperse them in the solvent, which is then placed in a vacuum filtration apparatus equipped with an ultrasonic probe to keep them from becoming agglomerated during deposition. Unlike the previously described process, when the mixture is vacuum deposited on to a porous substrate, such as one having a pore size up to the centimeter size, an electromagnetic field is applied to align the nanostructures during their deposition. This electromagnetic field can also be arbitrarily modulated in three space adjusted and to result in a woven or partially woven—partially nonwoven structure. The resulting membrane is then removed with the help of a supporting metal mesh and the entire membrane is immersed in acid to remove the initial substrate, which acted as a sacrificial support.

The vacuum filtration process may be modified to allow for the creation of multiple layers of nanostructures. A suspension of nanostructures can be formed in an organic solvent above a substrate. For example, with very low vacuum pressure the solvent is removed leaving behind a very thin layer of nanotubes on a steel mesh, such as a 20 micron steel mesh. This layer can then cured and dried. This process can repeated multiple times in order to create several layers of NanoMesh™.

Air Laid Manufacturing Process

In this process, nanostructures can be dispersed evenly, whether in a gas or a liquid solution. In a confined chamber, for example, a quantity of nanostructures is released as a fan to stir the gas to cause dispersion of the carbon nanotubes in the chamber. This gas may also be mechanically modulated at frequencies sufficient to cause dispersion. As the carbon nanotubes are being added to the chamber they are charged to a voltage sufficient to overcome the attractive Van der Waals forces, by passing the nanotubes through a high surface area electrode. This will prohibit agglomeration. The nanotube impregnated gas is now ready for gas phase deposition. By applying a pressure different passing the gas though a grounded mesh electrode. The nanotubes will stick to this grounded mesh electrode. At this point the carbon nanotube nanostructured material is in its most fragile state. The nanostructured material can now be exposed to ionizing radiation to cause the structure to fuse together and/or to coat surface via chemical vapor deposition (CVD), plasma enhanced chemical vapor deposition PECVD, or physical vapor deposition (PVD) processing techniques, or by chemical fusing techniques. The surface can then be removed and exposed to a sputtering process sufficient to cover the nanostructures and cause them to lock together. The resulting membrane can then be removed from the surface by reversing the charge of the surface causing the membrane to fall away.

Nanostructure Polymerization Process

In the polymerization process, a nanomaterial membrane is produced by linking nanostructures to one another through polymer bonding.

An envisioned process of this method involves first ultrasonicating a quantity of nanostructures (such as carbon nanotubes) in an acid solution. When using carbon nanotubes, the acid will act to cut the lengths of the nanotubes, to expose their ends, and allow carboxyl ions (COOH) to graft thereto. The resultant carboxyl functionalized product is then treated with concentrated acid to create carboxyl groups (COOH) which are more reactive for cross-linking reactions, such as condensation. This COOH functionalized nanostructure is then reacted at the carboxyl groups to cross-link two nanostructures together. The mixture is then allowed to react until an entire cross-linked network is formed into a fused nanomaterial membrane.

Method for Measuring Bacteria in Water

Multiple tests were performed on samples made using the methods generally described above using bacteria, such as *E. coli* bacteria and MS-2 bacteriophage. MS-2 is a male specific, single stranded RNA virus, with a diameter of 0.025 µm and an icosahedron shape. Its size and shape are similar to other water related viruses such as the poliovirus and hepatitis and it is a non-human pathogen.

The protocol used for testing removal of *E. coli* and MS-2 bacteriaphage and bacteria from water in the following examples were consistent with and generally adhered to: (i) Standard Operating Procedure for MS-2 Bacteriophage Propogation/Enumeration. Margolin, Aaron, 2001 University of New Hampshire, Durham, N.H. and (ii) Standard Methods for the Examination of Water and Wastewater, 20$^{th}$ Edition, Standard Methods, 1998. APHA, AWWA, WEF, Washington, D.C. These standards generally included the following procedure:

1) Placing the nanostructured material in a test housing designed to hold the nanostructured material to be challenged. Clamping the housing to prevent leakage of the challenge solution.
2) Connecting a sterile effluent tubing to a sterile Erilenmeyer flask using a rubber stopper.
3) Opening an influent port and introducing a challenge material through open port.
4) After introducing the challenge, closing the influent port, pumping, via a commercially available pump, a consistent flow through the effluent hose connected to the housing.
5) Pumping continued until all challenge material passed into the sterile Erlenmeyer flask, at which time the pump was turned off.
6) Placing 0.1 ml of challenge material in 9.9 mls of water or phosphate buffered saline solution (commercially available) in a 15 ml conical centrifuge tube.
7) Placing the 15 ml conical centrifuge tube into a commercially available vortex mixer and mixing it for about 15 seconds.
8) Removing about 0.1 ml of the mixture from the centrifuge tube and adding it to a second centrifuge tube containing 9.9 ml of water or phosphate buffered saline solution (commercially available), and repeating the vortex mixing described above.
9) Removing 0.1 ml of the mixture from the centrifuge tube and placing it on a tryptic soy agar (TSA) plate, (Remel Cat. No. 01917), where it can be spread with a sterile spreader over the agar surface. Drying the surface for 15 seconds before it is placed into a commercially available incubator at 36° C. and incubated for 18-24 hours.
10) After incubation, removing the plates from the incubator and placing them on a back lit plate counter. Counting those plates that appeared to have between 25-300 cfu/plate (1:10,000 dilution) per plate. The control and test plates were counted in the same manner.
11) Recording the number of virus or bacteria counted and the dilution factor at which they were counted, with an average of the plate counts being multiplied by their corresponding dilution factor and divided by the amount of dilution used per plate. This calculation, which is shown below, gives the amount of virus or bacteria in the original sample.

The following is a more detailed description of a procedure used in conducting testing with MS-2.

A 1% solution $MgCl_2$ (or $CaCl_2$) is first be prepared by adding to a desired amount of DI water $MgCl_2$ (or $CaCl_2$). A typical example is 1.0 g $MgCl_2$/99 ml DI water. This solution is autoclaved and cooled.

A preparation of Phosphate Buffered Saline Solution (1×PBS) is next prepared by adding to a desired amount of DI water Phosphate Buffered Saline Powder Concentrate. A typical example is 4.98 g PBS/500 ml DI water. This solution is also autoclaved and cooled.

A preparation of streptomycin/ampicillin antibiotic solution (Strep/Amp) is next made by adding to a desired amount of DI water Streptomycin Sulfate. A typical example is 0.15 g Strep/100 ml DI water. Ampicillin Sodium Salt is then added to the solution. A typical example is 0.15 g Amp/100 ml DI water. This solution is filtered thru 0.22 µm syringe filter into a sterile container.

A preparation of *E. coli* Stock Culture is made by first making a desired volume of Tryptic soy broth. The previously made streptomycin/ampicillin antibiotic solution is mixed with the T-soy in 1:100 ratio. (1.0 ml step/amp/100 ml T-soy).

Next 1% solution of $MgCl_2$ is added in 1:200 ratio. (0.5 ml $MgCl_2$/100 ml T-soy), followed by the addition of *E. coli* in 1:10 ratio. (10 ml *E. coli*/100 ml T-soy). The *E. coli* strain used herein is the HS(pF amp)R strain (*E. coli* with an inserted strep/amp resistance plasmid). *E. coli* strain C3000, which commercially available (American Type Culture Collection (ATCC)) can also be used.

The T-soy broth/*E. coli* culture is then placed into a shaking water bath at 37° C. (or orbital shaker in a 37° incubator), shaking vigorously for 2.5-3.0 hours (or at a time in which the *E. coli* reach mid-log phase in their growth cycle). This shaking step is to provide oxygen to the entire culture so it does not become anaerobic and inhibit growth. The culture is then from incubator and stored at 10° C.

MS2 Bacteriophage Propagation was performed by first adding liquid culture of MS2 (approx. $1 \times 10^{10} - 1 \times 10^{11}$ MS2/500 ml T-soy broth) to the T-soy broth and then incubating at 37° C. for 12-18 hours. The MS2 strain used was a commercially available specimen (ATCC (American Type Culture Collection), catalog #15597-B1).

The culture is transferred to an appropriate size centrifuge tube, and centrifuged under the following conditions: 10,000 rpm, 4° C., for 10 minutes. After centrifuging, the supernatant can be decanted, being careful not to disturb the pellet. The MS2 stock is generally stored at 10° C.

MS2 Enumeration is generally performed in the following manner. A 1× Overlay is made by mixing the following in 1000 ml of DI water and bringing to a boil.
 a. 15 grams T-soy broth
 b. 7.5 grams bacto agar
 c. 5 grams yeast extract
 d. 2.5 grams NaCl
 e. 0.075 grams $CaCl_2$ Four to Five ml of the overlay is next dispensed into test tubes and autoclave at 121° C. for 15 minutes, after which time the test tubes are removed from the autoclave and placed into 57° C. water bath for immediate use or stored at room temperature for future use. If placed in storage, the overlay will hardened, requiring it to be re-autoclaved. Overlay can only be re-autoclaved a few times until it becomes very dark, almost black, in color.

One skilled in the art would know how to perform 10 fold serial dilutions on sample in PBS to achieve a desired dilution point. Soon after remove the previously described test tube containing the overlay from the water bath, approximately 0.1 ml of the desired sample dilution and 0.2 ml of the previously described *E. coli* host can be fed is into the overlay. About 30 µL of the streptomycin/ampicillin antibiotic solution can be added for the mixed culture samples. It is important to note that the injection of 0.1 ml of diluted sample represents an additional 10 fold dilution. Therefore, when 0.1 ml of the $10^{-1}$ dilution is placed in the overlay, the resulting dilution on the T-soy plate is $10^{-2}$. In order to plate a $10^{-1}$ dilution, inject 0.1 ml of the original undiluted sample into the overlay. In order to plate a $10^0$ dilution, inject 1.0 ml of the original undiluted sample into the overlay using the same volume of the *E. coli* host (0.2 ml).

Without shaking, the diluted sample and MS2 is mixed throughout the overlay. The overlay and its contents are added onto a T-soy plate, which is swirled in a circular motion to evenly distribute the overlay across the surface of the agar. After a few minutes, the overlay harden, at which time it is incubated at 37° C. for 12-18 hours.

When the incubation is complete, MS2 plaques will appear as circular clearing zones in the *E. coli* lawn.

Negative and positive controls are generally used in this assay. The negative control includes the addition of only the *E. coli* to the overlay (no sample) to determine if the *E. coli* is growing properly, and if any phage or bacterial contamination is present. An additional control that can also be used to determine these factors can be performed by placing a small volume of the *E. coli* host (no MS2 or overlay) on a T-soy plate and examining the resulting colony morphology.

The positive control includes the addition of only the *E. coli* to the overlay (no sample) and subsequent plating. Once the overlay is evenly distributed across the surface of the plate, a small volume of MS2 stock is placed on various spots throughout the surface of the overlay. After incubation, the presence of plaques in these spots demonstrates that the *E. coli* host can effectively be infected by the MS2 phage.

Determining PFU/ml (Plaque Forming Units/ml) in original, undiluted sample:

$$PFU/ml = \frac{\text{\# of observed plaques on plate}}{\text{Dilution factor of the plate}}$$

For example, if 35 plaques were observed on a plate having a dilution factor of $10^{-8}$, the PFU would be:

$$\frac{35 \text{ plaques}}{10^{-8}} = 3.5 \times 10^9 \; PFU/ml \text{ in original sample}$$

Using the methods described above, and as exemplified in the following samples, there is strong adherence forces between bacteria and carbon nanotube, nanostructured material. The bacteria adhered to the carbon nanotube nanostructured material surface at sonication. It is believed that the same adherence of *E. coli* suspension occurs when it is passed through nanomesh of carbon nanotube nanostructured material.

In addition, it is believed that the integrity of the bacteria cell is destroyed upon interaction with carbon nanotube, nanostructured material. For example, bacteria tests using the nanostructured material described herein showed a destructive mechanism in which the shell/cell wall was completely destroyed. This destruction apparently occurs due to a breech in the integrity of the cell wall, which leads to a catastrophic failure of the cell wall, due to the difference in the osmotic pressure between the interior of a complete cell and the osmotic pressure on the exterior of the cell. Thus, when the integrity of the cell wall/shell is compromised, those osmotic pressure differences result in disintegration of the bacteria.

For example, Example 3 shows the destruction of *E. coli* bacteria, as evidenced by the presence of free bacteria DNA and protein found in the filtrate. Damaged cells are dissipated by water flow as seen in Example 3. Therefore, not only does the inventive carbon nanotube nanostructured material completely destroy bacteria but the inventive material does not foul due to the build up of bio burden, which should provide for a longer life than those materials currently used.

The invention will be further clarified by the following non-limiting examples, which are intended to be purely exemplary of the invention.

EXAMPLE 1

Fabrication of an Activated Defective Nanostructured Material

An activated nanostructured material was made from commercially available purified carbon nanotubes. These nanotubes were placed in a 50 ml conical centrifuge tube to which concentrated nitric acid was added to a volume of 45 ml. The tube was shaken vigorously for 2-3 minutes to mix the acid and nanotubes, and then centrifuged at 2,500 RPM for five minutes to pellet the nanotubes.

A yellow supernatant was decanted and the nitric acid wash was repeated. The carbon nanotubes were then washed 2-3 times with water to reduce the acid concentration below a point at which the acid did not react with the isopropanol used in the following steps.

100 mg of the nitric acid washed/water rinsed carbon nanotubes were next added to 400 ml of commercially available neat isopropanol and ultrasonicated in a Branson 900B ultrasonicator 80% power until the carbon nanotubes were well dispersed (about 10 minutes). The mixture was further diluted by adding 2 liters isopropanol such that the total volume of the resulting mixture was 2.4 liters. This diluted mixture was ultrasonicated for an additional 10 minutes.

Next, 800 mg of a commercially available 200 nm diameter silicon oxide nano-fiber was homogenized in a commercially available blender at full power for 10 minutes in 500 ml of the commercially available neat isopropanol. The homogenized mixture was then diluted by adding an additional 1 liter of commercially available neat isopropanol.

The previously prepared mixture of carbon nanotubes and silicon oxide nano-fiber was mixed and then quantity sufficient (Q.S.) amounts of isopropanol was added to obtain 4 liters. This 4 liter solution was then ultrasonicated with a "Branson 900B ultrasonicator" at 80% power for 15 minutes, which caused the carbon nanotube nanomaterial to uniformly disperse.

The entire 4 liter solution was then deposited onto a 16 square inch area on a commercially available 5 micron polypropylene nonwoven fused fabric. About half of the solution was passed through the polypropylene fabric under ½ in Hg of vacuum pressure. The remaining 2 liters of the solution was then passed through the fabric under a pressure of 5 in Hg until the remaining solution passed through the polypropylene fabric and the carbon nanotube silicon oxide suspension was deposited on the fabric.

The resulting nanostructure material (called NanoMesh™) was removed from the fabricator and allowed to air dry at room temperature for 2 hrs to form an activated carbon nanotube, nanostructured material.

EXAMPLE 2

Purification Test of Nanostructured Material with *E. coli* Bacteria

This example describes a purification test on water contaminated with *E. coli* bacteria stock culture, that was purchased from American Type Culture Collection (ATCC).

A bacteria assay was conducted by challenging the carbon nanotube nanostructured material, made in accordance with Example 1, with a challenge of (($4\times10^7 \pm 2\times10^7$ colony forming units per ml (cfu/ml)) of *E. coli* stock culture ATCC #25922, that was first reconstituted. Using a sterile biological loop (commercially available) a loop of the reconstituted stock was removed and streaked on a commercially available blood agar plate and incubated for 12-18 hours at 36° C. The culture was then removed from the incubator and examined for purity.

Using a sterile biological loop (commercially available) a loop of the incubated culture was removed and placed in 10 ml of sterile commercially available Tryptic soy broth (Remel cat. No. 07228). *E. coli* was then grown in the resulting trypticase-soy broth overnight to form a stock culture of $1\times10^9$ cfu/ml. 1 ml of the stock culture was added to 100 ml of water used for the challenge test. The resulting challenged water was then passed through the carbon nanotube, nanostructured material, made in accordance with Example 1.

The test was performed in accordance with the "Standard Methods for the Examination of Water and Waste Water" cited above. Results of tests following the protocols described above established consistent removal of *E. coli* bacteria greater than 6 logs (>99.99995%) to greater than 7 logs (>99.999995%) when the challenge material was passed through the carbon nanotube, nanostructured material, made in accordance with Example 1.

The test results established removal rates which exceeded EPA potable water standards for removal of bacteria from water. The EPA standards dictate 6 logs removal (>99.99995%) of *E. coli* bacteria to achieve potable water. Improved purification by greater log removals of *E. coli* bacteria have been achieved in such tests, by challenging the carbon nanotube, nanostructured material, with higher concentrations of *E. coli* bacteria challenge material, made as described above. Such tests with higher concentrations confirm removal rates of greater than 7 log. Independent tests, using the test procedures described in this example, of the carbon nanotube nanostructured material, made in accordance with Example 1, establish this material as a complete barrier to *E. coli* bacteria.

EXAMPLE 3

Chemical Analysis of Sterilized Post-Challenge Filtrate

This example describes the chemical analysis of filtrate from an *E. coli* challenge test, performed as described in Example 2, on the carbon nanotube nanostructured material, made in accordance with Example 1. This example provided verification of purification through destruction of *E. coli* bacteria passing through the inventive carbon nanotube nanostructured material. Evidence of purification through the destruction of the contaminant, (*E. coli* bacteria) was established by the presence of DNA and protein in the challenge filtrate.

A challenge test was run in accordance with Example 2, except that the composition of the challenge material was $1\times10^8$ cfu/ml of *E. coli*. A total of 100 ml (total=$1\times10^{10}$ cfu) of this challenge solution was drawn through the carbon nanotube, nanostructured material using with ½ in Hg of vacuum pressure. A control filtrate was obtained by passing the *E. coli* challenge filtrate through a commercially available 0.45 micron Millipore filter. The resulting filtrates, of the control and the challenge, were then analyzed with a commercially available spectra-photometer to determine the presence of protein and DNA. The test challenge filtrate was not concentrated. However, the analysis of the filtrate with a commercially available spectra-photometer revealed 40 µg/ml of DNA and 0.5 mg/ml of protein. Concentrations of protein and DNA at these levels in non-concentrated challenge filtrate were 6 times higher than the control test material. These concentrations confirmed the destruction of the *E. coli* in the challenge by the carbon nanotube nanostructured material.

EXAMPLE 4

Purification Test on Water Contaminated with MS-2 Bacteriophage Virus

This example describes a purification test on water contaminated with MS-2 bacteriophage virus using the procedure described above and in the "Standard Operating Procedure for MS-2 Bacteriophage Propagation/Enumeration, Margolin, Aaron, 2001, An EPA Reference Protocol." The MS-2 bacteriophage virus is commonly used in assessing treatment capabilities of membranes designed for treating drinking water (NSF 1998). The pressure challenges for this example were performed with 100 ml challenge solutions using the protocols described above. The MS-2 challenge materials were prepared in accordance with those steps enumerated above.

In this test, eighty (80) membranes comprised of the carbon nanotube nanostructured material made in accordance with Example 1, were challenged. The challenge material used was water contaminated with MS-2 bacteriophage virus to the concentration of $4\times10^6 \pm 2\times10^6$ pfu/ml.

Of the 80 units tested, 50 units achieved MS-2 removal of 5 logs (99.999%) or greater than 5 logs (>99.9995%). The remaining 30 units demonstrated 4 logs (99.99%) or greater than 4 logs (>99.995%) removal of MS-2. While EPA standards recommend 4 logs removal of MS-2 Bacteriophage to achieve potable water, it is believed that better sensitivity (higher log removal) can be achieved by challenging with higher log challenges of MS-2. Improved purification by greater log removals of MS-2 Bacteriophage have been achieved in such tests, by challenging the carbon nanotube nanostructured material, made in accordance with Example 1, with higher concentrations of MS-2 Bacteriophage challenge material, made as set forth above. Independent tests of the carbon nanotube nanostructured material, made in accordance with Example 1, establish this material as a complete barrier to MS-2 Bacteriophage.

EXAMPLE 5

Purification Test on Water Contaminated with Arsenic (As)

This example describes a purification test on water contaminated with arsenic. In this test, a stock solution of 150 parts per billion arsenic in 100 ml of water was passed through the carbon nanotube, nanostructured material, made in accordance with Example 1. A sample of the as-treated water was analyzed according to the EPA Method #SM 183113B. The analysis of the challenge filtrate confirm a reduction of the arsenic level by 86%±5%; after passing the challenge as-treated water, one time through the inventive carbon nanotube nanostructured material.

EXAMPLE 6

Removal of Contaminants from Aircraft Fuel

A sample of contaminated jet fuel (JP8) was obtained from a 33,000 gallon storage tank located at the United States Air Force Research facility at the Wright Patterson Air Force base. After collection, the sample was cultured on trypticase-soy agar and found to contain three types of bacteria: two *bacillus* species and one *micrococcus* species. The sample was separated in two container of 2 liters each. Both containers presented two distinct layers, jet fuel on top and water on the bottom. Container A contained a heavy contaminated growth layer at the interface between the water and the fuel. Container B only showed slight contamination. The challenge test bacteria were obtained from the interface of the fuel and water from Container B.

After being homogenized, which was accomplished by shaking the challenge test fuel/water/bacteria vigorously for 1 minute, 200 ml of the fuel/water/bacteria challenge mixture was passed one time, using 3 inches of Hg of vacuum pressure, through the carbon nanotube, nanostructured material, made in accordance with Example 1.

The fuel/water/bacteria challenge filtrate sample was allowed to separate into its fuel-water components, and four test samples were obtained from each component. Each test sample was plated on agar. Samples were then incubated to analyze bacteria growth at 37° C. and samples were incubated at room temperature to analyze mold growth. No bacteria or mold culture growth was observed on the challenge filtrate test plates after incubating the samples for 24 and 48 hours. The control samples presented vigorous colonies of bacteria and mold growth after incubation at 24 and 48 hours. The results confirm that the carbon nanotube nanostructured material, made in accordance with Example 1, was a complete barrier to bacteria in fuel for it accomplished removal of bacteria and mold from the fuel beyond the limits of measuring with testing protocols.

EXAMPLE 7

A Study of *E. coli* Interaction with Carbon Nanotube Nanostructured Material

The carbon nanotube nanostructured material, made in accordance with Example 1 was rinsed 6 times with DI water. The rinsed carbon nanotube nanostructured material was diluted to a concentration of 10,000 ppm in DI water.

Preparation of *E. Coli* Suspension

A culture of *E. coli* as described above, was prepared to a concentration of $5\times10^9$ CFU/ml in pure water.

Preparation of Control Slide Sample #1:

One drop of the prepared *E. coli* suspension was placed on a commercially available glass microscope slide (American Scientific Products, Micro Slides, plain, Cat. M6145, size 75×25 mm) that was cleaned with sulfuric acid and rinsed with DI water. The drop of *E. coli* suspension was smeared and allowed the to air dry, and refrigerated at 4 degrees Celsius for 48 hours. The prepared slide was heat fixed by passing through a flame in a manner known to the art.

Preparation of Test Suspensions:

The remaining *E. coli* suspension, prepared as outlined above, was then divided in two equal parts by separating into two Erlenmeyer flasks (Suspension #1 and #2).

Preparation of Suspension #1:

Suspension #1 was diluted with DI water to a concentration of $2\times10^9$ CFU/ml of *E. coli*.

Preparation of Suspension #2:

Carbon nanotube, nanostructured material, made in accordance with Example 1, was added to Suspension #2. Suspension #2 was diluted with DI water to the same concentration of *E. coli* as Suspension #1. The concentration of carbon nanotube nanostructured material, made in accordance with Example 1, was 625 ppm.

Ultrasonication and Centrifuging:

Suspensions #1 and #2 were simultaneously ultrasonicated with a Branson-2510 sonicator for 3 min. These suspensions were centrifuged in a commercially available centrifuge at 2500 rpm for 2 minutes to pellet them, and subsequently decanted leaving 1 ml of supernatant behind (and to suspend the pellet in Suspension #1 and #2). The pellet of Suspension #1 and #2, was then used in samples described below.

Sample #2:

Sample 2 was prepared by placing a drop of Suspension #1 was placed on a glass slide described above, and refrigerated for 19 hours. After being refrigerated for 19 hours, an atomic force microscope (AFM) was used to investigate the sample without fixation. Sample #2 was then placed in a refrigerator for 24 hours at the same temperature noted above. After being refrigerated for 24 hours, Sample #2 was thermally fixed, by methods know in the art. Sample #2 was stained by methods know to the art, using with Gram Crystal Violet dye. Light microscopy was subsequently investigated.

Sample #3:

Sample 3 was prepared by placing (and smearing) a drop of Suspension #2 on a glass slide. Thermal fixation was performed within 3 hours after ultrasonic treatment. Stain Sample #3, by methods know to the art, using Gram Crystal Violet dye. Sample #3 was placed in a refrigerator at the same temperature noted above. After 19 hours, Sample #3 was removed from the refrigerator and analyzed with an AFM without fixation. Sample #3 was placed back in the refrigerator at for 24 hours, after which time light microscopy was conducted.

Sample #4:

Sample #4 was prepared in the manner described for Sample #2, with the exception that Suspension #2 (and not Suspension #1) was used.

Light Microscopy

Samples were investigated under Olympus light microscope at 1000× magnification and under immersion oil. Digital images were made with Olympus DP10 CCD.

Figure 2:
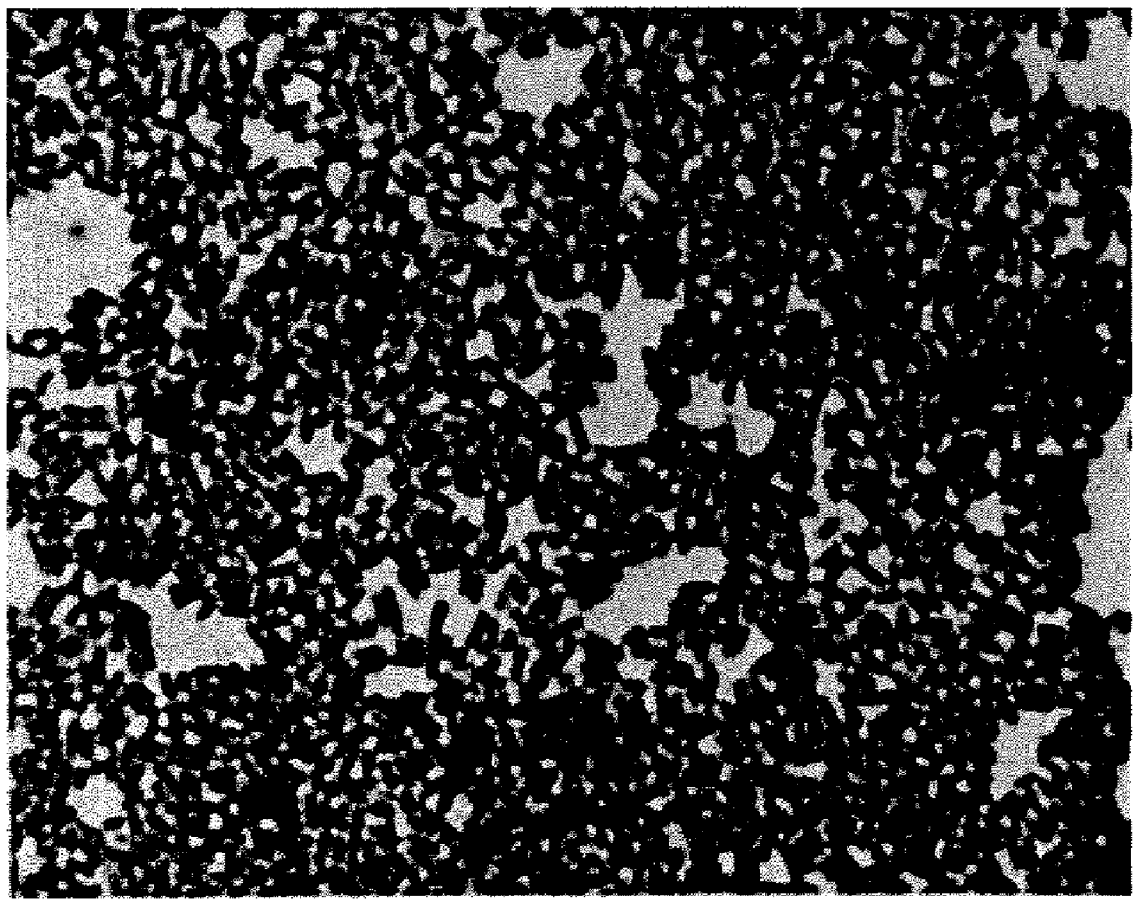
FIG. 2 is an optical image of sample 2: *E. coli* without carbon nanotube, nanostructured material (sonicated; fixation after 48 hours).

Both samples #1 and #2 (suspension of bacteria without carbon nanotube nanostructured material) demonstrated the image of *E. coli* cells uniformly distributed over the entire surface of the slide (see FIGS. 1 and 2). The images illustrate bacteria as having well-defined edges suggesting that the bacteria cells were intact. No changes in their shape were found after 2 days stored in a dry state in the refrigerator. There were no detectable changes in bacteria cell morphology between samples that were heat fixed and stained 3 hours after sample preparation or heat fixed and stained after 2 days stored in a dry state in the refrigerator.

Figure 3:
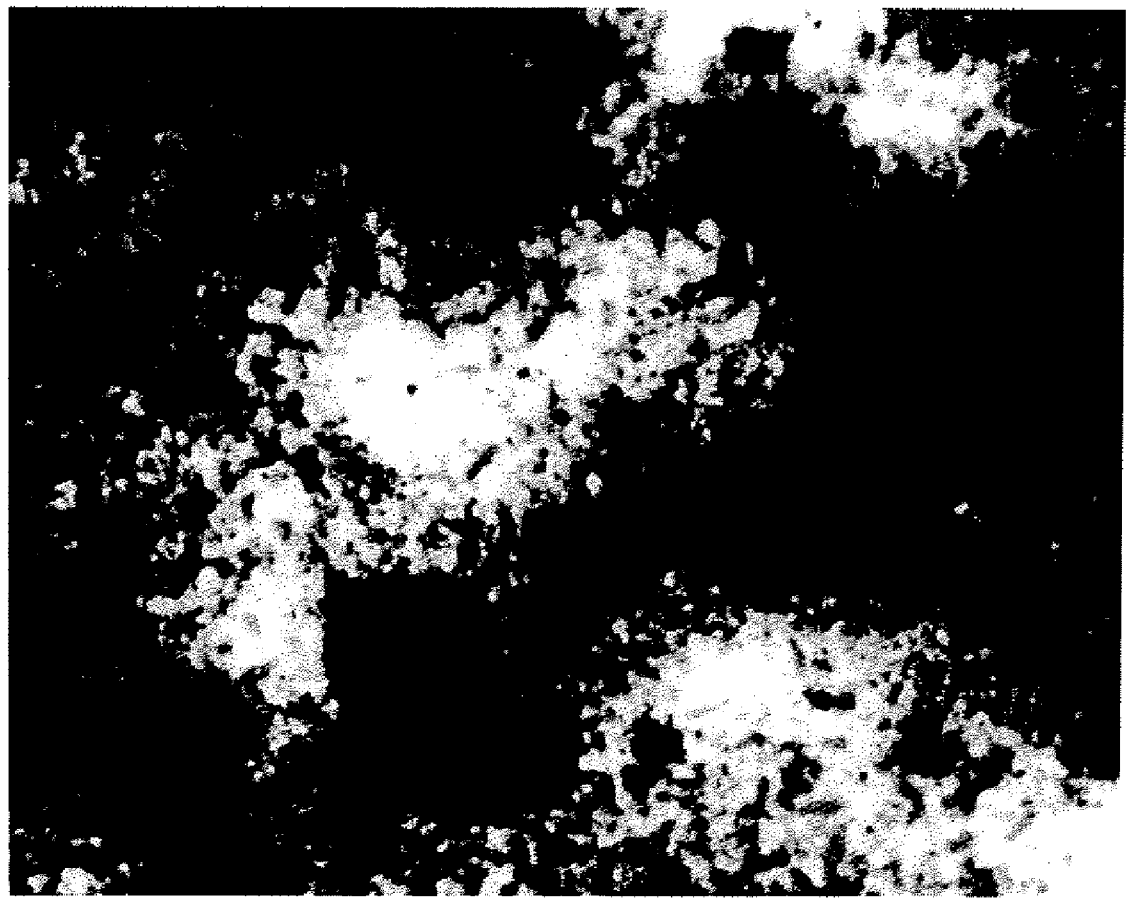
FIG. 3 is an optical image of sample 3: *E. coli* with carbon nanotube, nanostructured material; sonicated; fixation within 3 hours.

Sample #3 demonstrated complete absence of bacteria on the areas of the slide where no nanotubes were observed. There were only a few carbon nanotube nanostructured material observed at the periphery of the smear. The majority of the carbon nanotube nanostructured material had been washed from the slide when the excess violet stain was washed from the slide. Bacteria concentration was observed at boundaries of carbon nanotube nanostructured material (FIG. 3). The bacteria areas separate particles as shown in violet.

Figure 4:
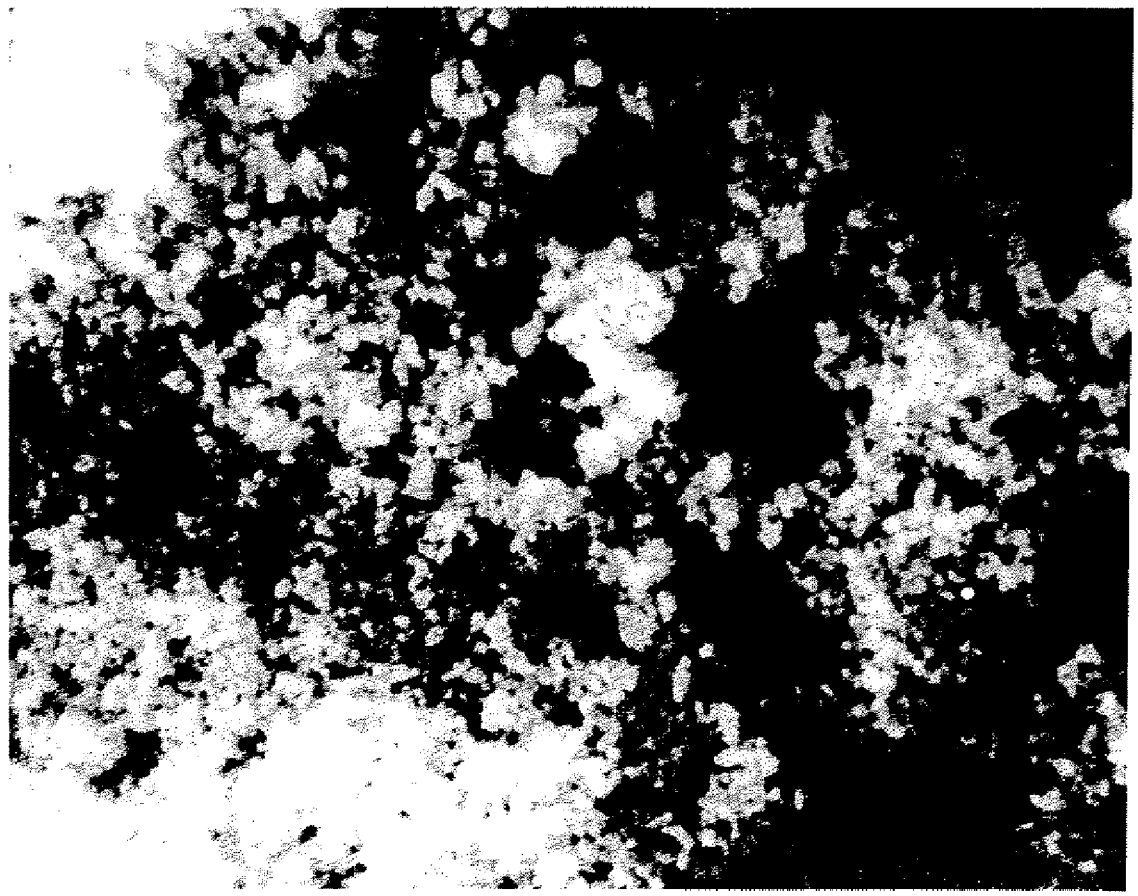
FIG. 4 is in optical image of sample 4: *E. coli* with carbon nanotube, nanostructured material (sonicated; fixation after 48 hours).

Sample #4 also demonstrated presence of *E. coli* at boundaries of carbon nanotube nanostructured material but it appear in the image as blur spots (FIG. 4).

Atomic Force Microscopy Analysis

Atomic force microscopy (AFM) was made at Veeco Dimension 3100 Scanning Probe System in tapping mode.

Figure 5:
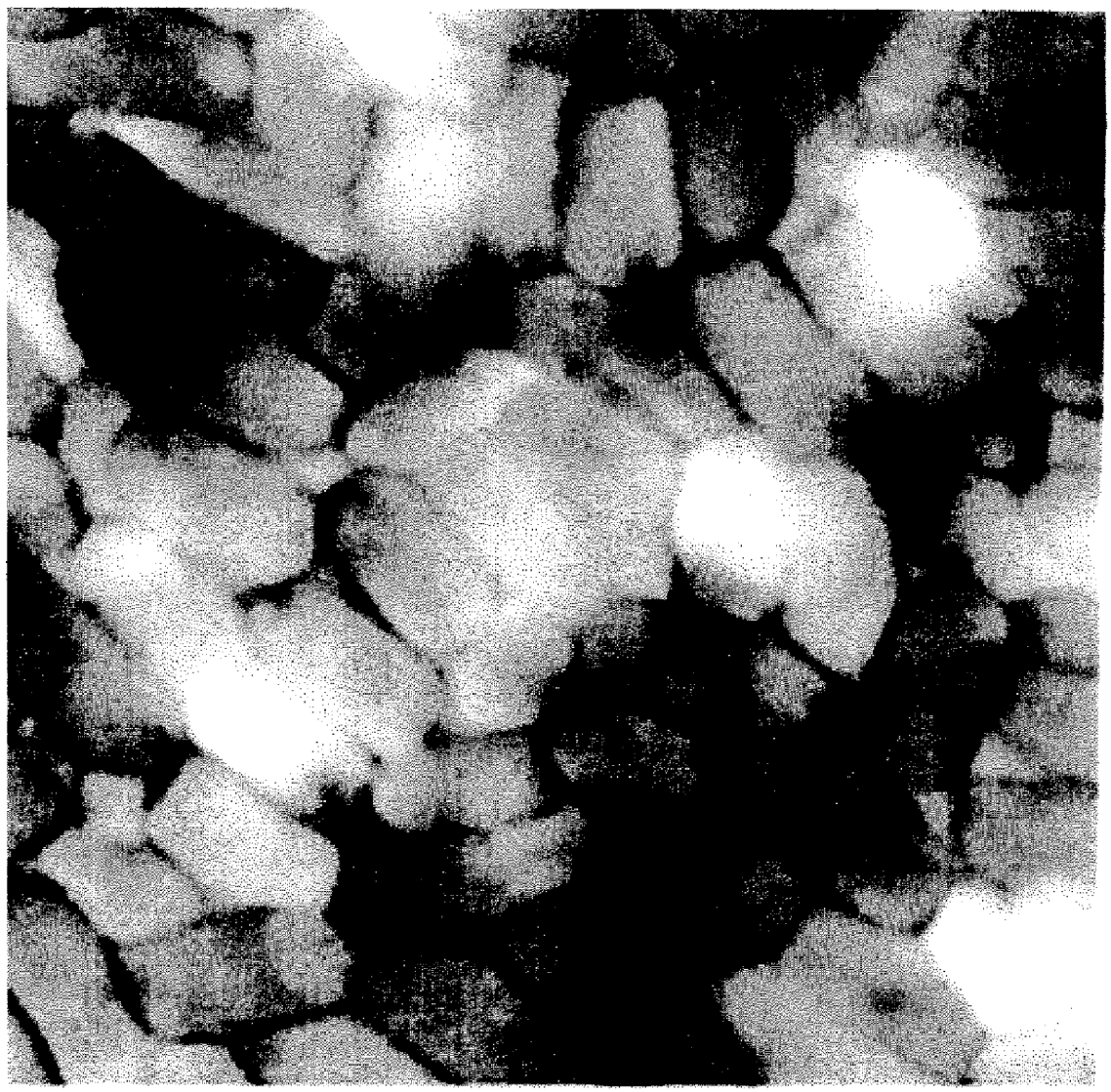
FIG. 5 is in an AFM image of sample 2: *E. coli* without carbon nanotube, nanostructured material (sonicated; no fixation).

Sample #2 demonstrated *E. coli* closely packed together (FIG. 5). All cells had sharp boundaries. Note that the decrease in size and packing density of bacteria can be seen when comparing AFM image of sample #2 before heat treatment (FIG. 5) and optical image of this sample after heat treatment (FIG. 2).

Figure 6:
FIG. 6 is an AFM image of sample #3: *E. coli* with carbon nanotube, nanostructured material (sonicated; fixation within 3 hours).

Sample #3 shows some cells inside of carbon nanotube nanostructured material (FIG. 6). The presence at least one individual cell in upper middle part of the image is apparent. The boundary of the *E. coli* cell wall is diffused.

Figure 7:
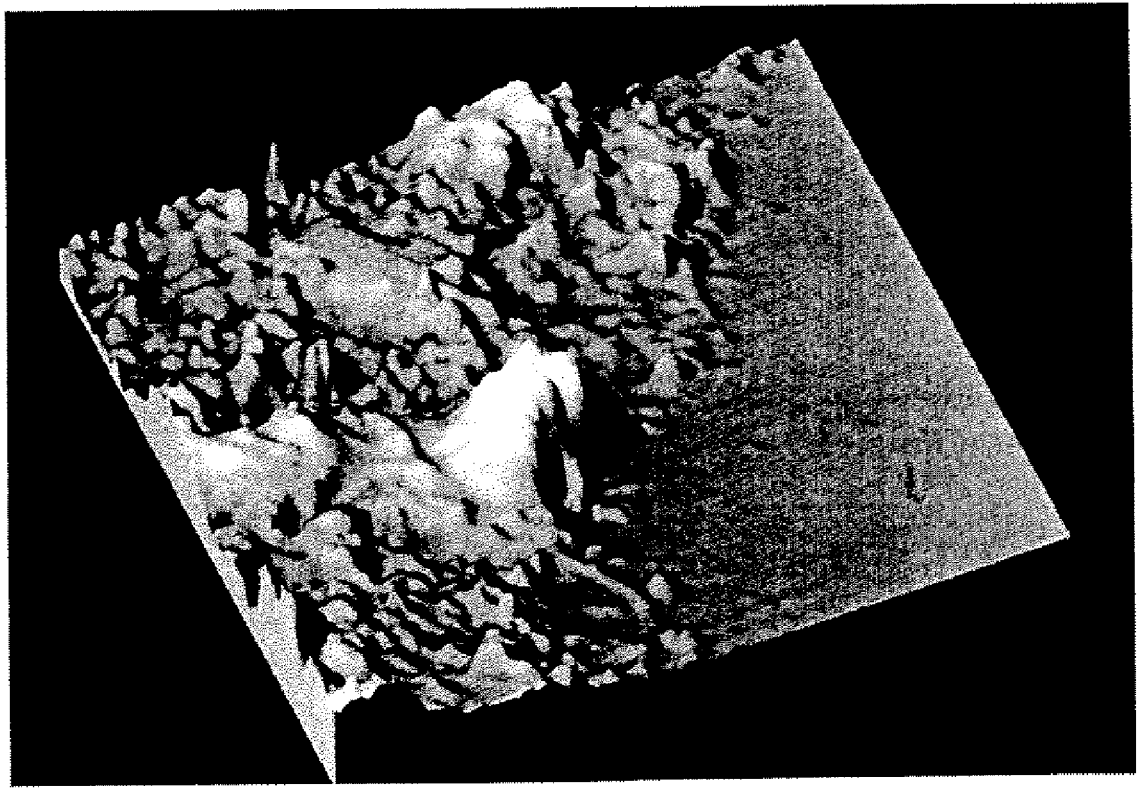
FIG. 7 is an AFM image of sample #3: three dimension transformation of FIG. 6.

The disintegrating structure of the *E. coli* cell is also recognizable in 3D image (FIG. 7). Also, we can see some diffused material within the carbon nanotube nanostructured materials.

Figure 10:
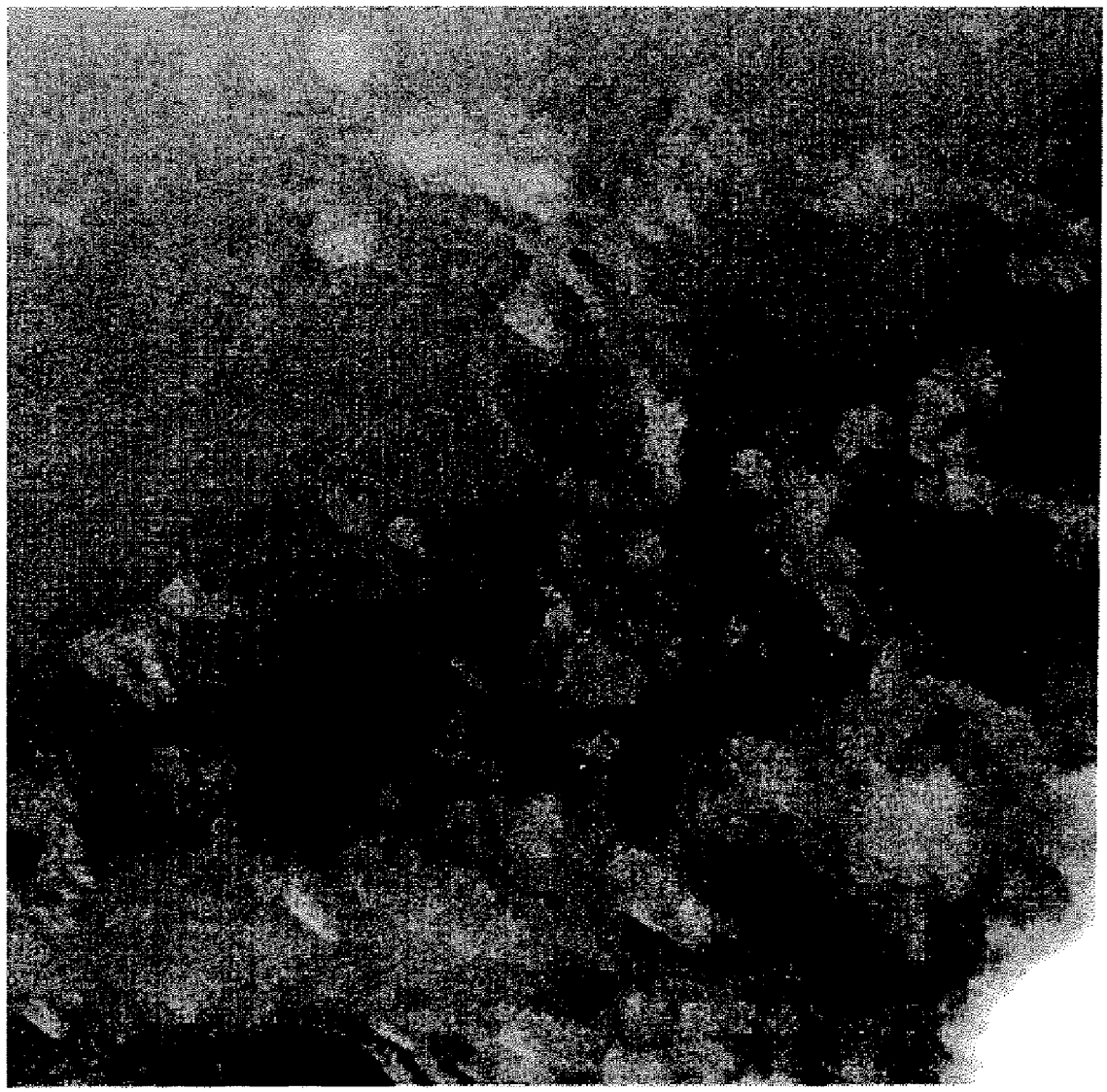
FIG. 10 is AFM image of Sample #4: *E. coli* with carbon nanotube, nanostructured material (sonicated; no fixation).
Figure 11:
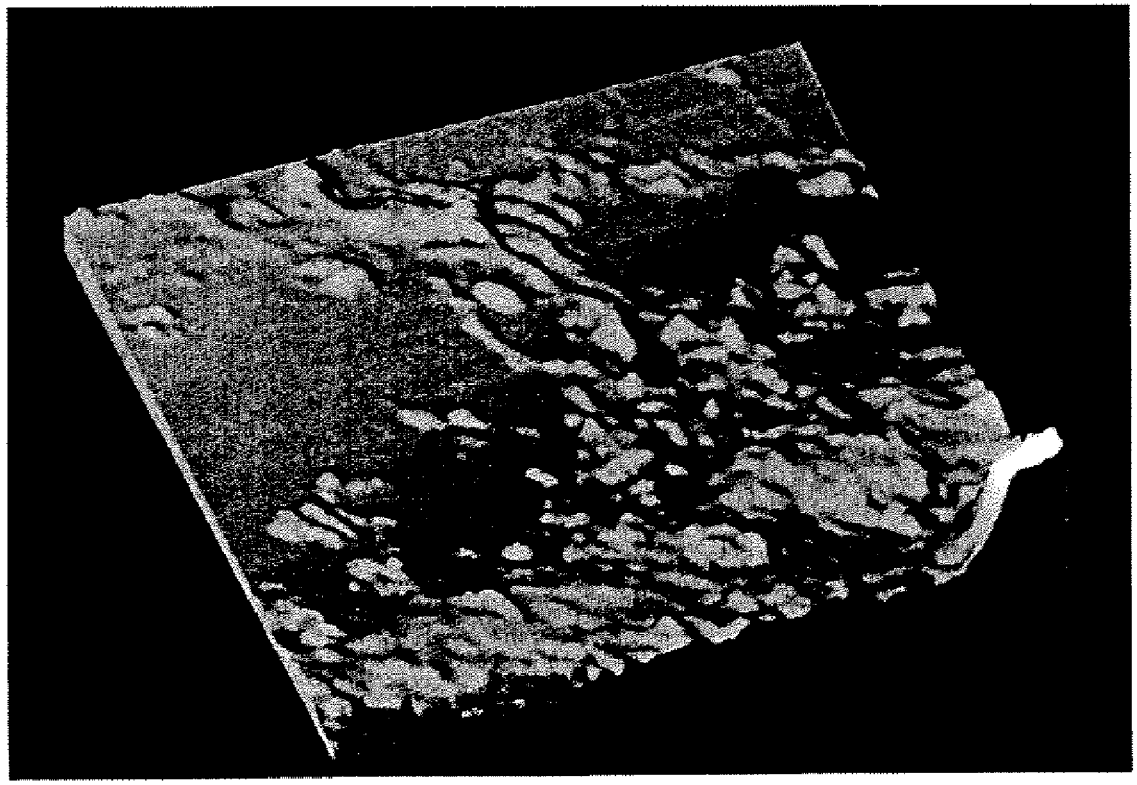
FIG. 11 is an AFM image of sample #4: three dimension transformation of FIG. 10.
Figure 12:
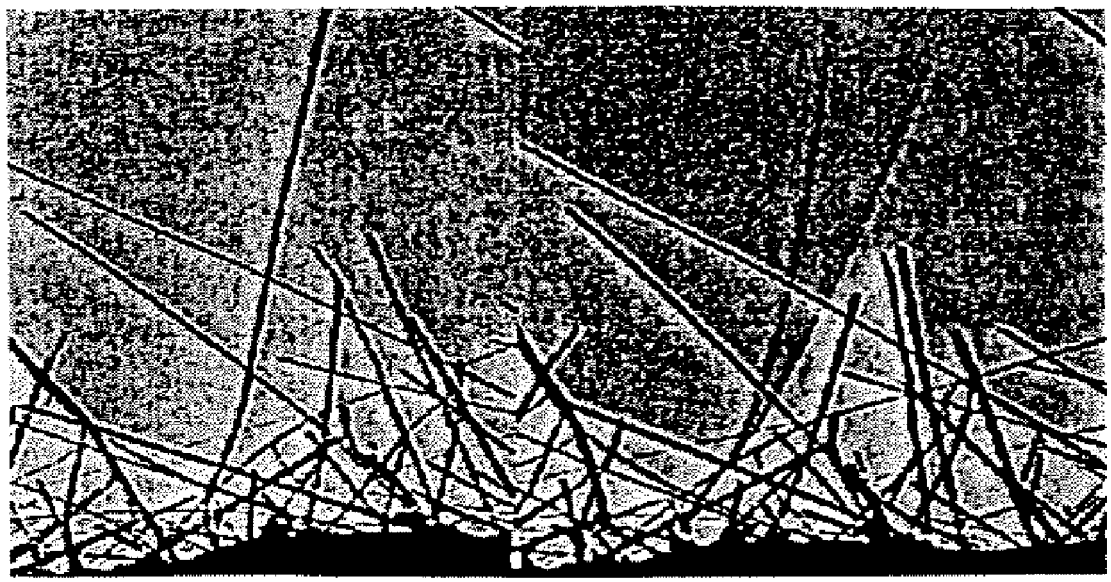
FIG. 12 is a photograph showing a vertical nanotube at rest (left) and vibrating (right) due to fluid flow.
Figure 13:
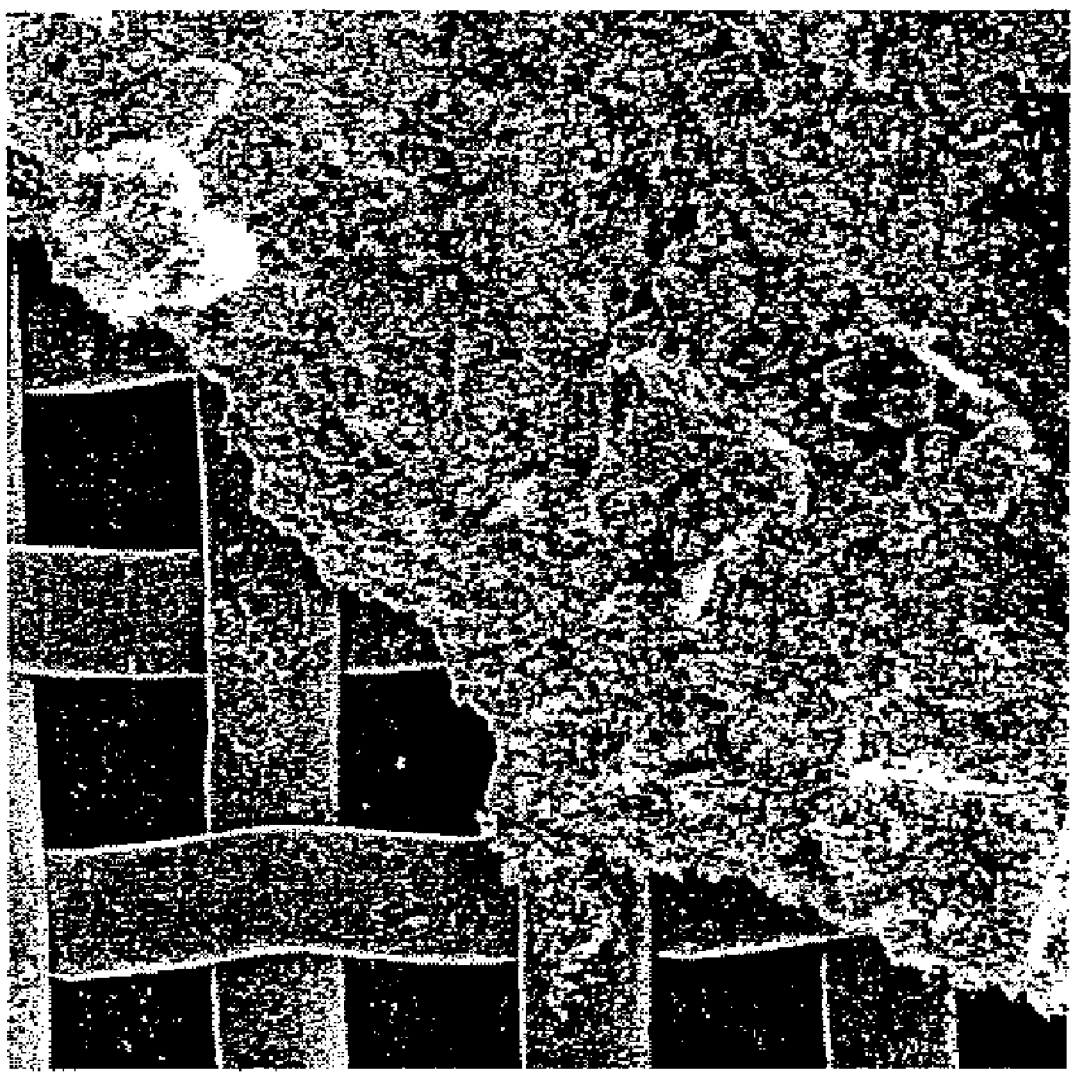
FIG. 13 is a micrograph of the edge of a nanostructured material attached to a 20 micron metal mesh superstructure.
Figure 14:
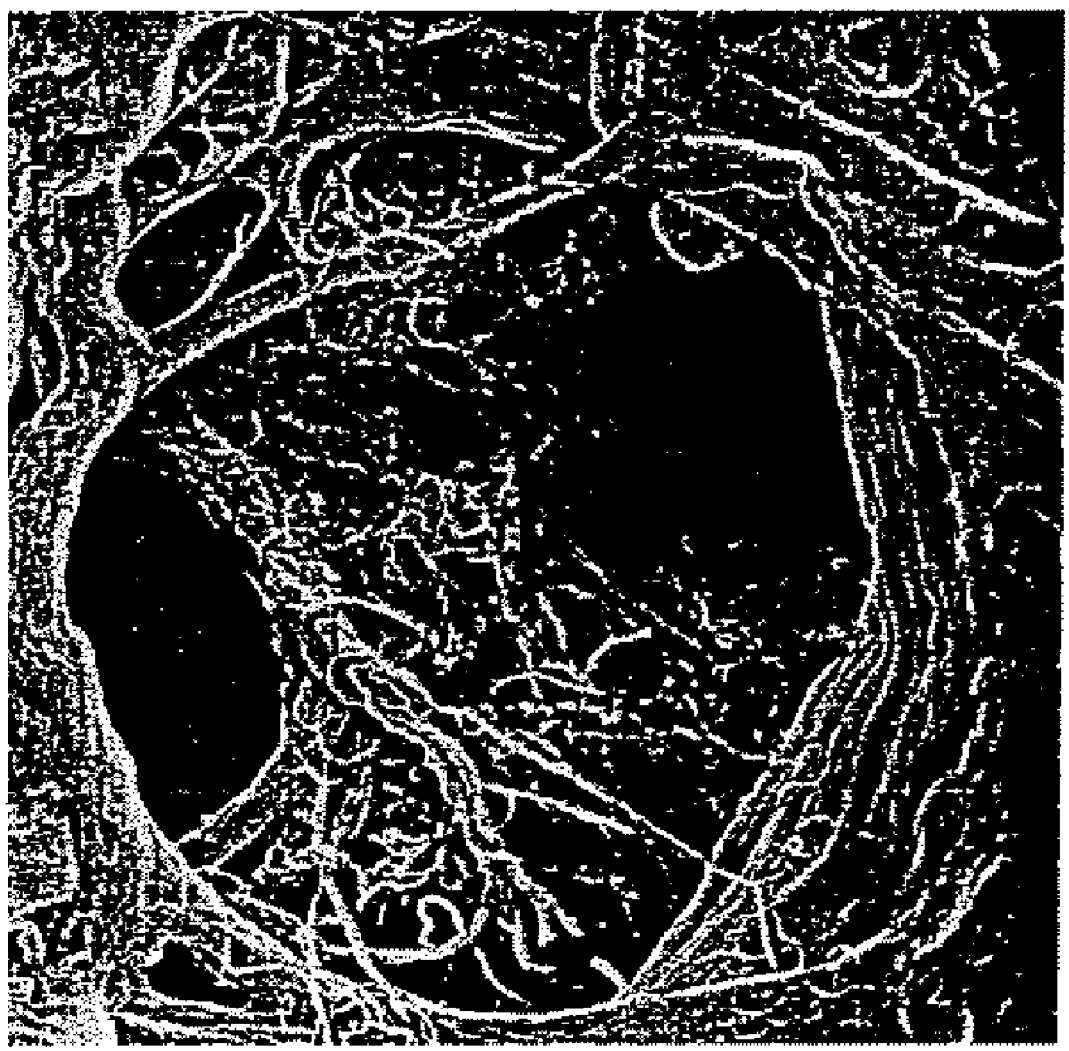
FIG. 14 is a micrograph showing nanotubes in a pore of a supporting superstructure (cellulose acetate) wrapping themselves around the fibers of the support structure.
Figure 15:
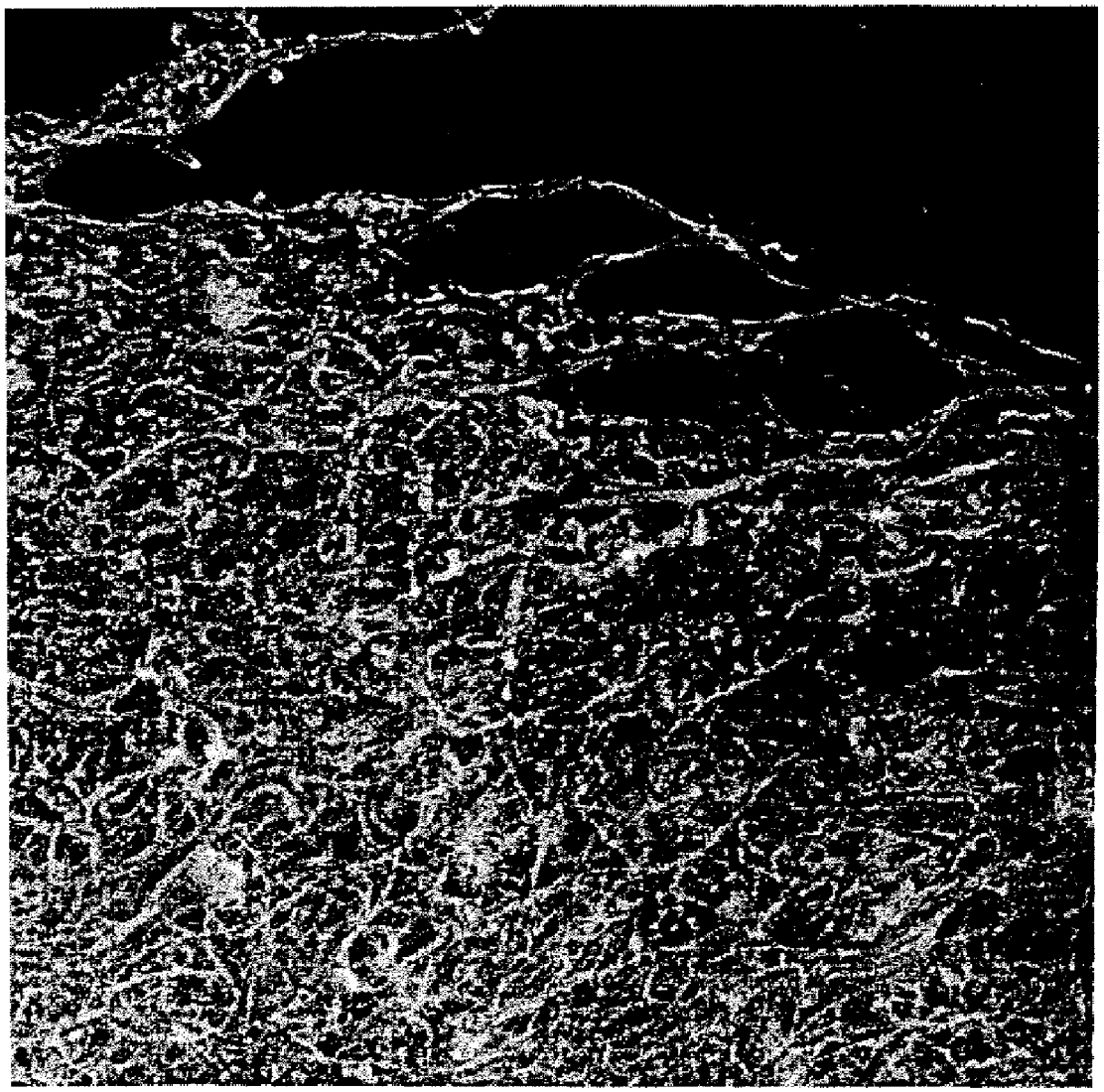
FIG. 15 is a micrograph of the torn edge of a carbon nanotube nanostructured material.
Figure 16:
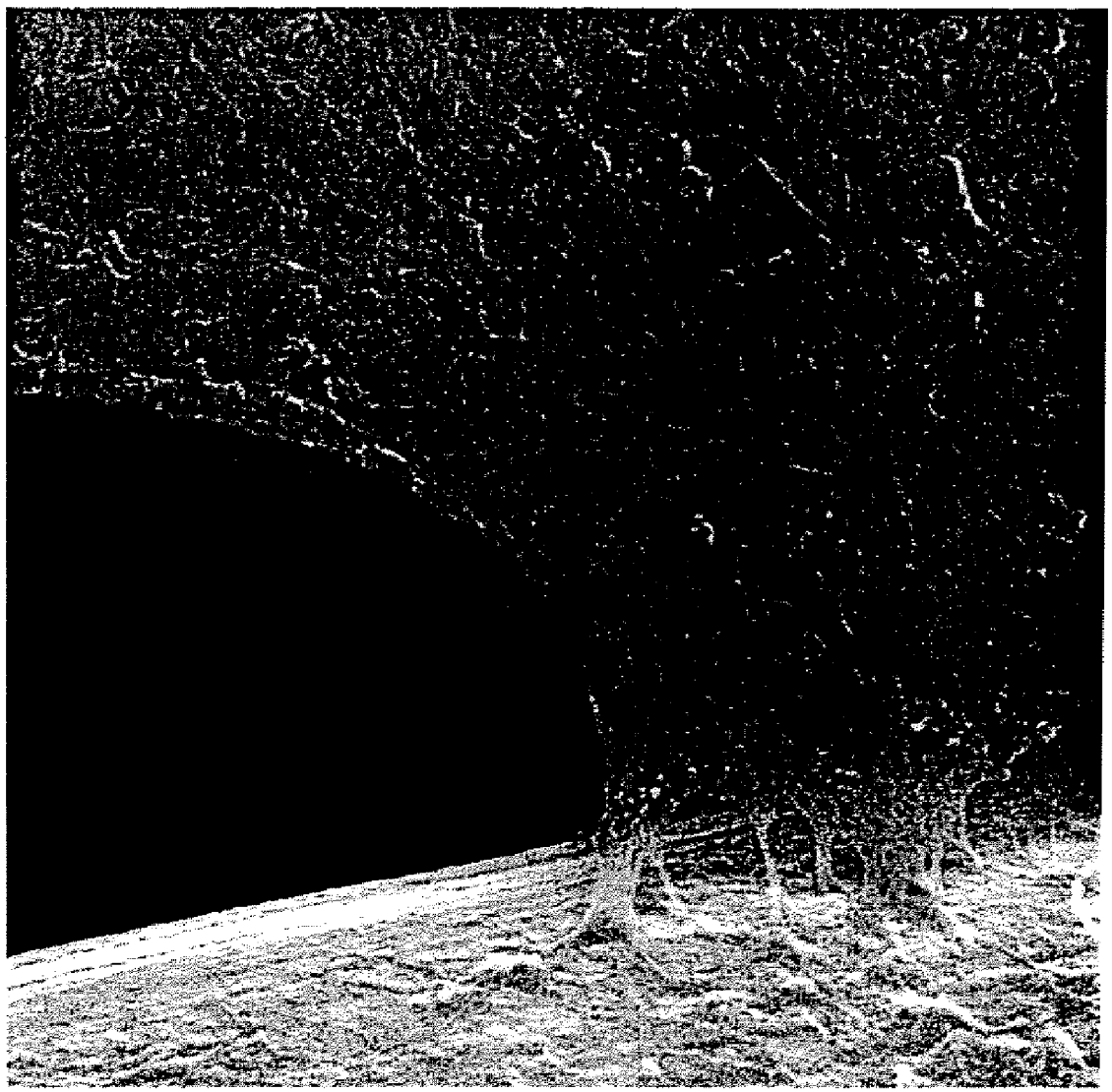
FIG. 16 is a micrograph of a fused monolayer of carbon nanotube nanostructured material stretched and fused to support wires spanning a 25×25 micron opening.
Figure 17:
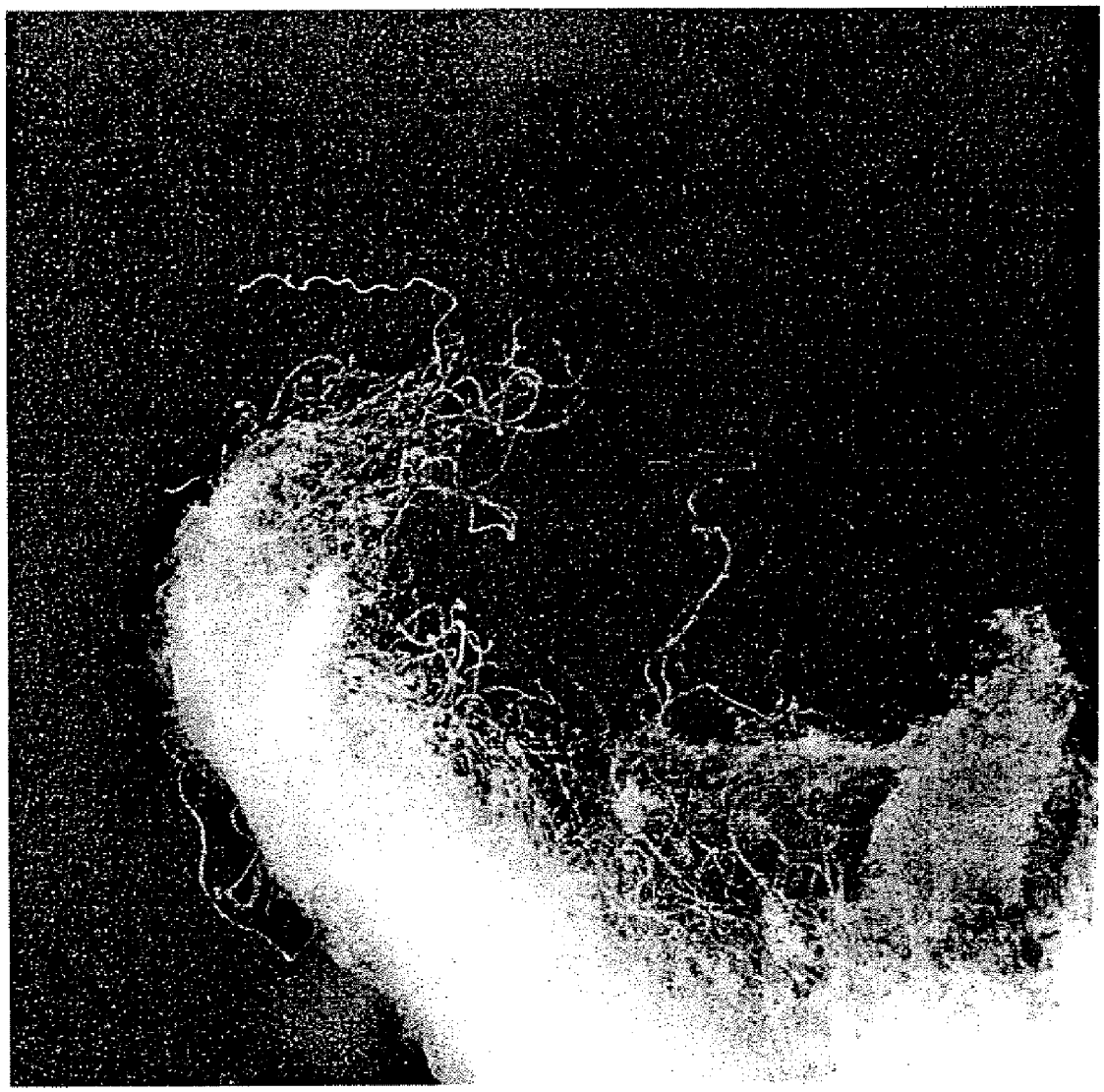
FIG. 17 is a photograph of self woven carbon nanotube nanostructured material.
Figure 18:
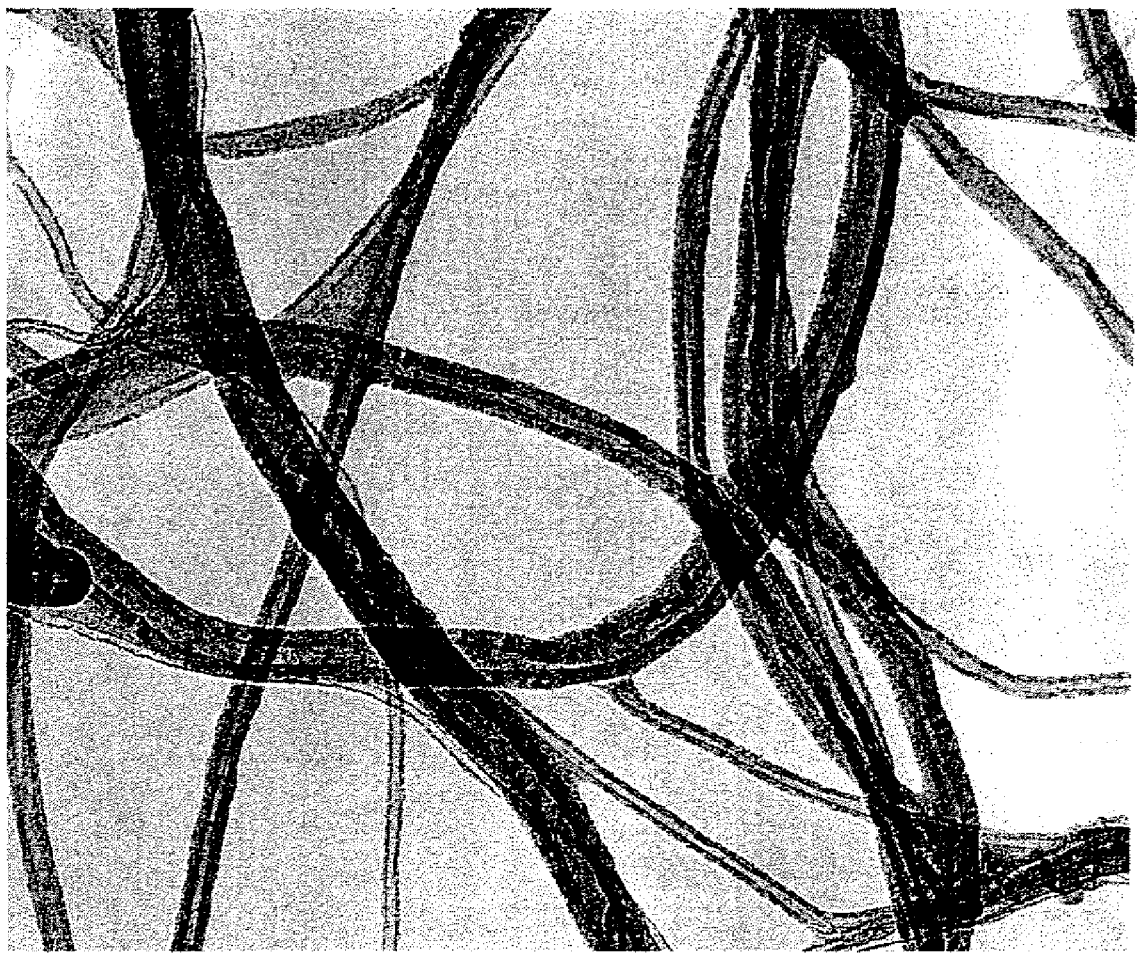
FIG. 18 is a micrograph of freestanding carbon nanotubes fused at the intersection points to form a nanostructured material.
Figure 19:
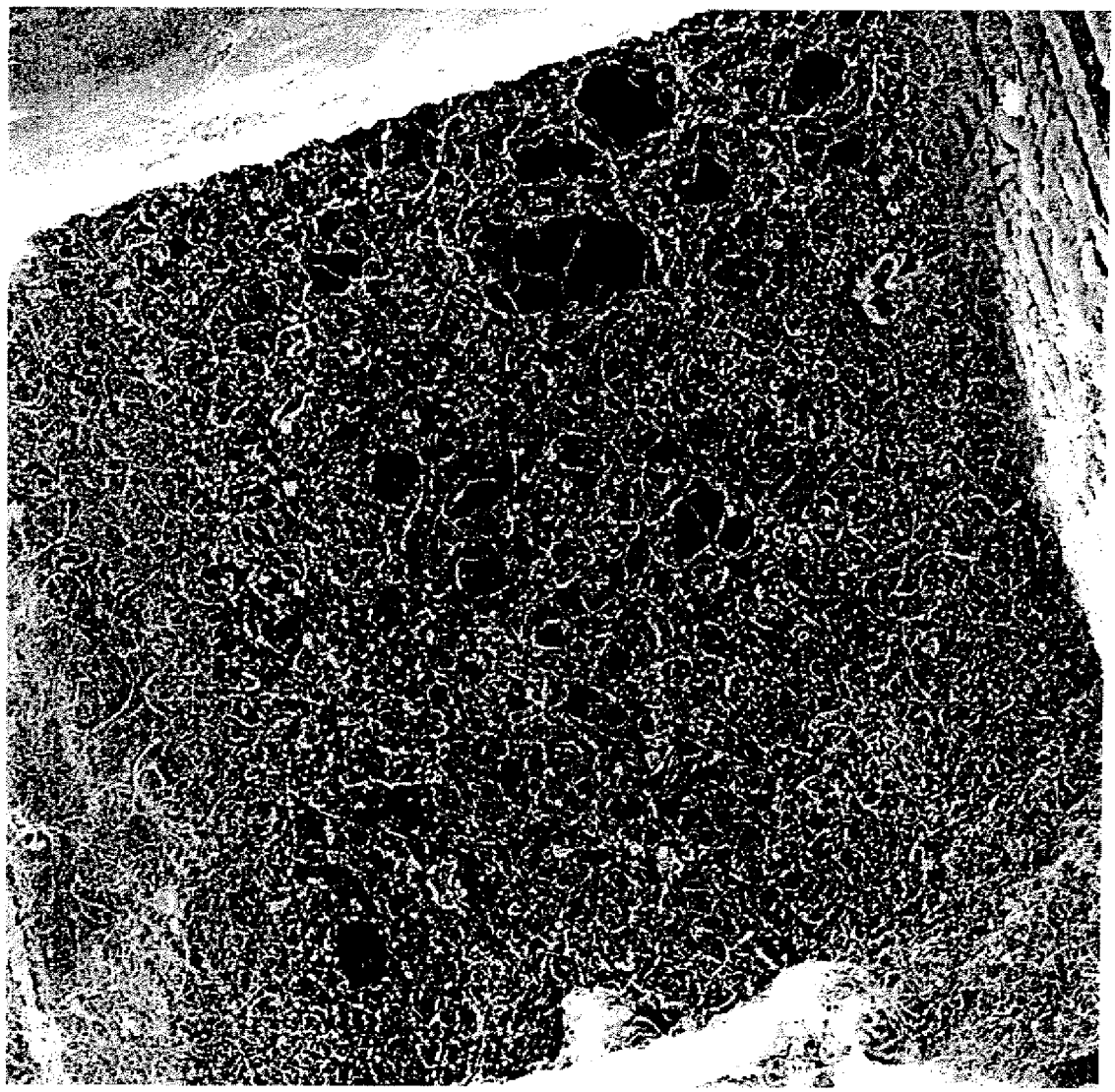
FIG. 19 is a micrograph of freestanding, self woven nanostructured material.
Figure 20:
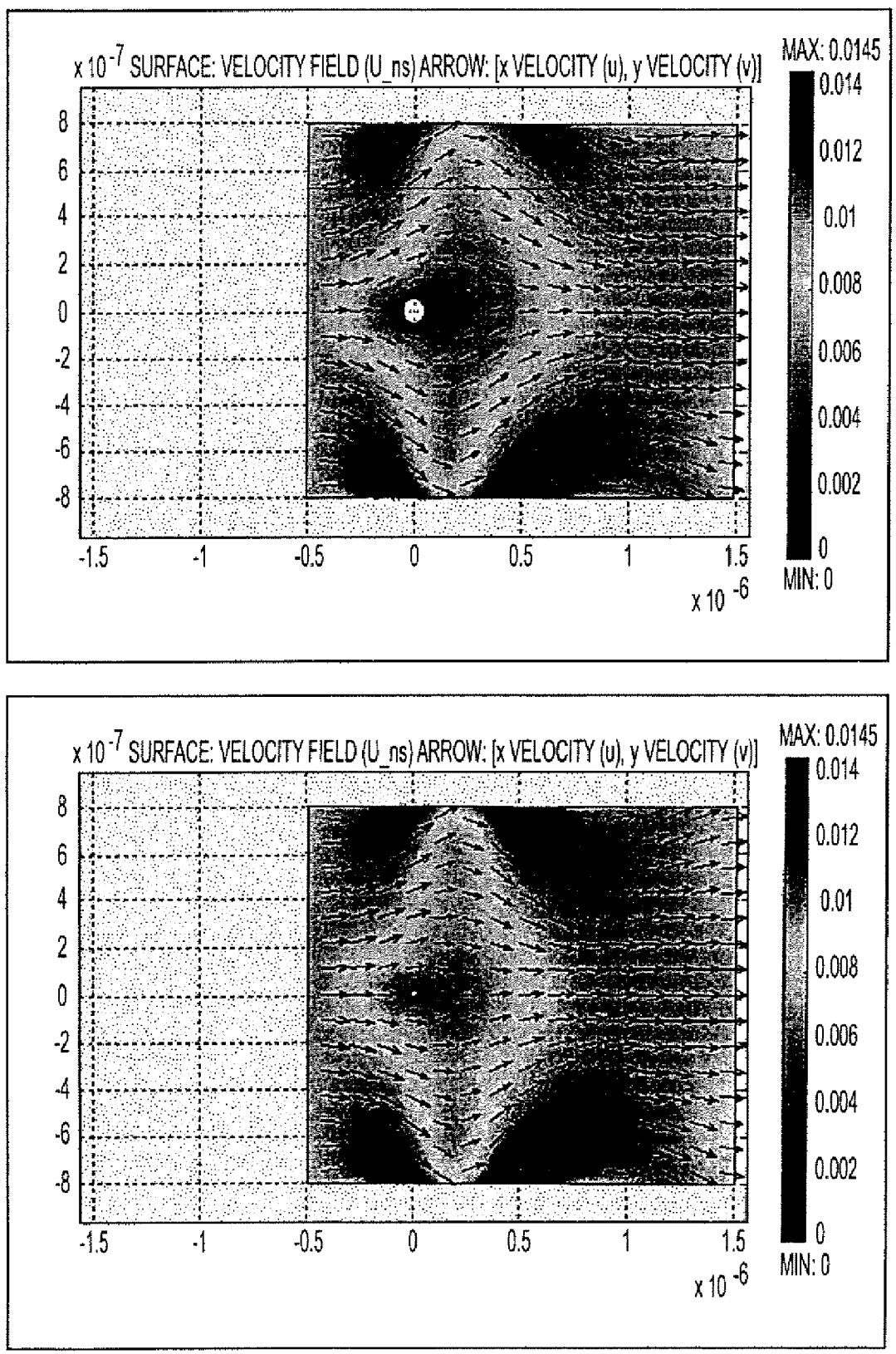
FIG. 20 is a simulation of fluid flow dynamics around a carbon nanotubes in a nanostructured material.
Figure 21:
FIG. 21 is an image showing the results of a bacteria removal test.

A larger surface area of sample #4 than is shown in FIG. 10 was investigated and all of the *E. coli* cells are disintegrated beyond the point of recognition. However we can see the presence of diffused *E. coli* fragments within the carbon nanotube nanostructured material.

On ultrasonication in DI water of, *E. coli* and carbon nanotube nanostructured material, the two components agglomerated due to electrostatic and Van Der Waals forces. To the limit of detection, it was observed that all bacteria in suspension were in contact with carbon nanotube nanostructured material, and adhered. There were no longer free *E. coli* cells in Suspension #2.

Figure 8:
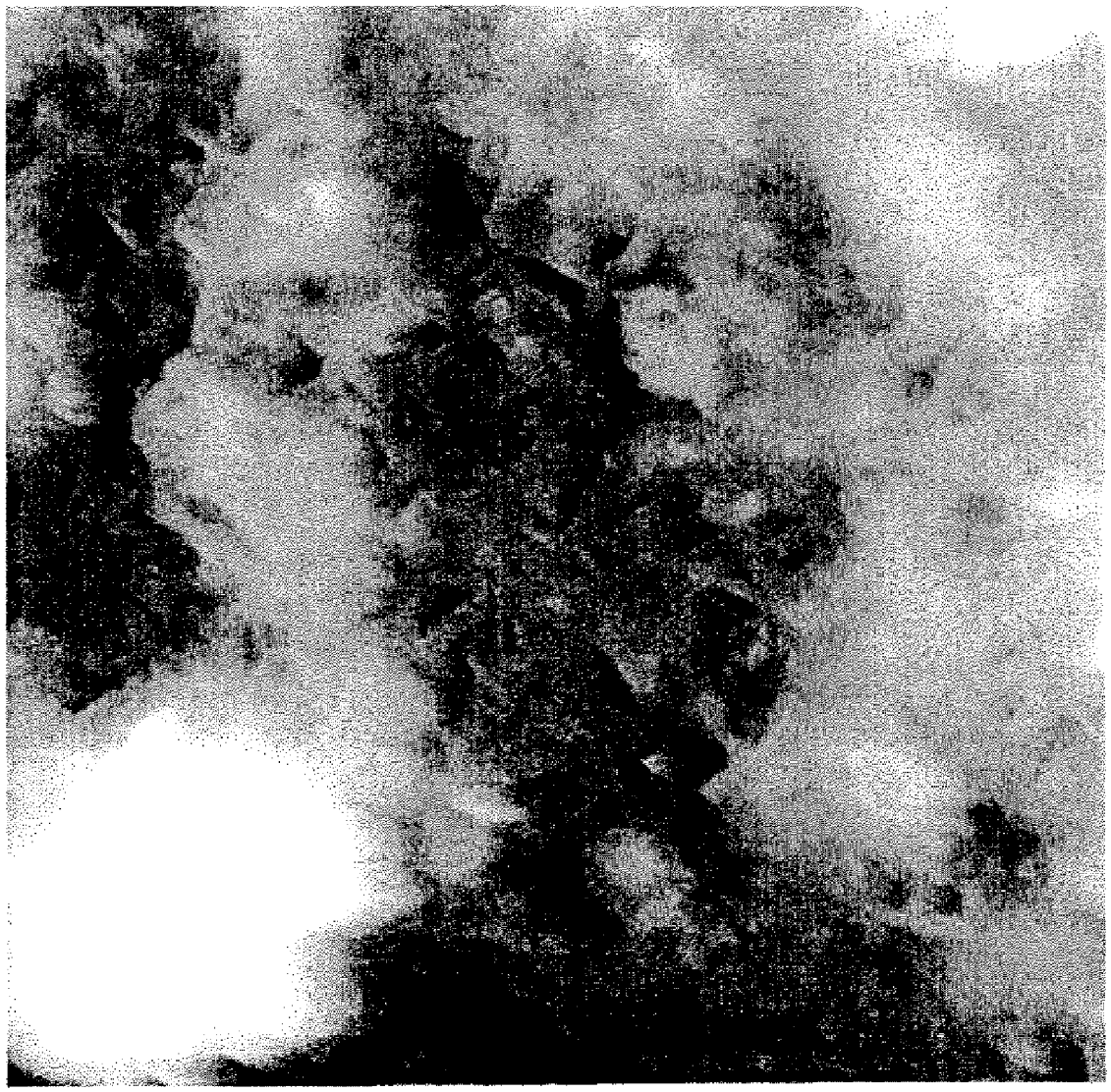
FIG. 8 is an AFM image of sample #3: *E. coli* with carbon nanotube, nanostructured material (sonicated; fixation within 3 hours).
Figure 9:
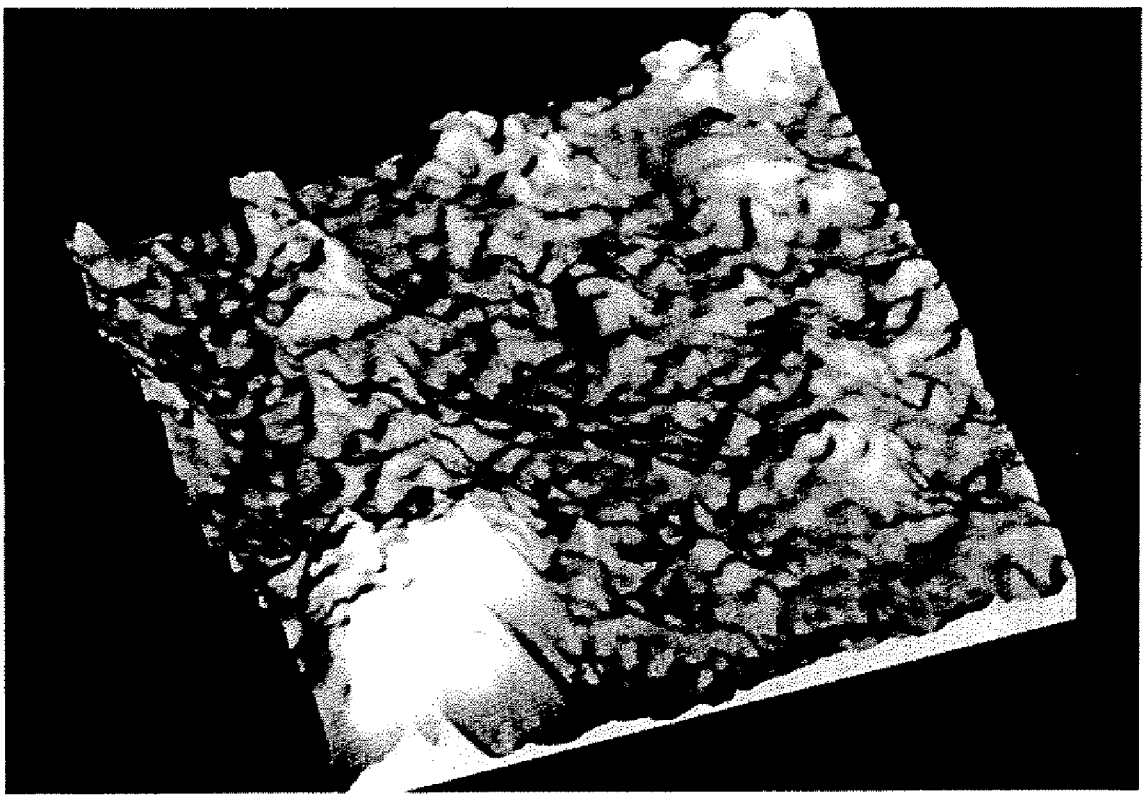
FIG. 9 is an AFM image of sample #3: three dimension transformation of FIG. 8.

The disintegration of the *E. coli* cells started immediately, or soon after the cells come into intimate contact with the nanotubes. As a result, the bacteria appeared to loose their sharp boundaries and the internal contents of the bacteria appeared to spread out of the cell. The beginning of this process resulted after 3 hours of fixation (FIGS. 6 and 8), and after 22 hours the spread went so far that it is difficult to recognize individual bacteria (FIG. 10).

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is

1. An article for reducing or removing at least one contaminant from a fluid, said article comprising:
  (a) a filtration media comprising:
    carbon nanotubes having at least one functional group attached thereto, and a support medium for said carbon nanotubes, wherein a plurality of said carbon nanotubes are fused or bonded to said support medium, to another carbon nanotube, or to a combination thereof, and
  (b) an assembly containing said filtration media.

2. The article of claim 1, wherein the filtration media is permeable to flow of said fluid.

3. The article of claim 1, wherein the filtration media is positioned in said assembly to allow contaminated fluid to flow through and/or adjacent to said filtration media.

4. The article of claim 1, wherein said support medium comprises ceramic, metal, or polymeric materials, which may be in the form of fibers, substrates, and particles.

5. The article of claim 4, wherein said polymeric material comprises single or multi-component polymers, nylon, polyurethane, acrylic, methacrylic, polycarbonate, epoxy, silicone rubbers, polystyrene, polyethylene terephthalate, polybutylene terephthalate, poly-paraphylene terephtalamide, poly-(p-phenylene terephtalamide), polyester ester ketone, viton fluoroelastomer, poly-tetrafluoroethylene, polyvinylchloride, polyester, polypropylene, polychloroprene, acetates, and combinations thereof.

6. The article of claim 4, wherein said ceramic material is chosen from at least one of the following: boron carbide, boron nitride, boron oxide, boron phosphate, spinel, garnet, lanthanum fluoride, calcium fluoride, silicon carbide, carbon and its allotropes, silicon oxide, glass, quartz, aluminum oxide, aluminum nitride, zirconium oxide, zirconium carbide, zirconium boride, zirconium nitrite, hafnium boride, thorium oxide, yttrium oxide, magnesium oxide, phosphorus oxide, cordierite, mullite, silicon nitride, ferrite, sapphire, steatite, titanium carbide, titanium nitride, titanium boride, and combinations thereof.

7. The article of claim 1, wherein said carbon nanotubes further comprise at least one lattice distortion.

8. The article of claim 1, wherein said functional group comprises at least one organic functional group, inorganic functional group, or combinations thereof.

9. The article of claim 1, wherein said filtration media is electrically conductive or electrically charged.

10. The article of claim 1, said article further comprising a device to stimulate said filtration media with static or dynamic electromagnetic fields.

11. The article of claim 10, wherein the filtration media contain intrinsic or externally supplied electrical potentials that introduce or augment the removal efficiency of at least one contaminant.

12. A method of reducing or removing at least one contaminant from fluid, said method comprising passing fluid through an article comprising:
(a) a filtration media comprising:
carbon nanotubes having at least one functional group attached thereto, and a support medium for said carbon nanotubes,
wherein a plurality of said carbon nanotubes are fused or bonded to said support medium, to another carbon nanotube, or to a combination thereof, and
(b) an assembly containing said filtration media,
wherein said filtration media is positioned in said assembly such that the fluid passes through or adjacent to said filtration media to capture said at least contaminant in said filtration media,
wherein said at least one contaminant is chosen from salts, metals, pathogens, microorganisms, DNA, RNA, natural organic molecules, molds, fungi, natural and synthetic toxins, endotoxins, proteins, and enzymes.

13. The method of claim 12, wherein said at least one contaminant in the fluid is captured by the said filtration media under one set of conditions and subsequently released under a different set of conditions.

14. The method of claim 13, wherein said different set of conditions result from changing electric fields, magnetic fields, thermal fields or any combination thereof.

15. The method in claim 12, wherein the said fluid is chosen from water, air, fuel, biological fluids, and food stuffs.

16. The method of claim 15, wherein said fluid comprises water, and said contaminants in said water are reduced to an amount sufficient to obtain potable water, water for injection, industrial pure water, or purified waste water.

17. The method of claim 11, wherein said microorganism is chosen from bacteria, virus, cysts, parasites or a combination thereof.

18. The method of claim 17, wherein when said microorganism comprises virus or cyst, or combinations thereof, said method reduces their concentration by at least 99.99%.

19. The method of claim 17, wherein when said microorganism comprises bacteria or parasites, or combinations thereof, said method reduces their concentration by at least 99.9999%.

20. The method of claim 17, wherein when said at least one contaminant is an endotoxin, said method reduces the concentration of said endotoxin to a concentration below 0.25 EU/ml.

21. The method of claim 12, further comprising stimulating said filtration media with static or dynamic electromagnetic fields while said contaminated fluid is in contact with said filtration media.

* * * * *